US006359196B1

(12) United States Patent
Lok et al.

(10) Patent No.: US 6,359,196 B1
(45) Date of Patent: Mar. 19, 2002

(54) GERMINATION-SPECIFIC PLANT PROMOTERS

(76) Inventors: Finn Lok, Kongshaven 15, Copenhagen-Valby DK-2500; Ole Olsen, Holmbladsgade 102, 2TV., Copenhagen S DK-2300; Per-Johan Meijer, Holsteinsgade 50, 5 TV., Copenhagen DK-2100; Verena Cameron-Mills, Kirkevaenget 20, Valby DK-2500, all of (DK)

( * ) Notice: Subject to any disclaimer, the term of this patent is extended or adjusted under 35 U.S.C. 154(b) by 0 days.

(21) Appl. No.: 09/404,390

(22) Filed: Sep. 23, 1999

(51) Int. Cl.$^7$ .......................... A01H 1/00; C07H 21/04; C12N 5/14; C12N 15/00

(52) U.S. Cl. .......................... 800/278; 435/6; 435/419; 435/320.1; 536/23.1; 536/24.1; 536/24.3; 800/288

(58) Field of Search .................. 435/6, 419, 320.1; 536/23.1, 24.1, 24.3; 800/278, 288

(56) References Cited

U.S. PATENT DOCUMENTS

| | | |
|---|---|---|
| 5,712,112 A | 1/1998 | Yu et al. |
| 5,763,252 A | 6/1998 | Skadsen et al. |

OTHER PUBLICATIONS

Abe, M. et al. (1994), *J. Biochem.*, 116:488–492 "Corn Crystatin I Expressed in *Escherichia coli*: Investigation of Its Inhibitory Profile and Occurrence in Corn Kernels."

Abe, M. et al. (1996), *Biosci. Biotech. Biochem.*, 60(7):1173–1175 "Structural Organization of the Gene Encoding Corn Cystatin."

Bevan, Michael (1984), *Nucleic Acids Research*, 12(22):8711–8721 "Binary *Agrobacterium* vectors for plant transformation."

Brown, W. M. et al. (1997), *Protein Science*, 6:5–12 "Friends and relations of the cystatin superfamily—new members and their evolution."

Bruce, W. B. et al. (Dec. 1989), *Proc. Natl. Acad. Sci. USA*, 86:9692–9696 "Photoregulation of a phytochrome gene promoter from oat transferred into rice by particle bombardment."

D'Halluin, K. et al. (Dec. 1992), *The Plant Cell*, 4:1495–1505 "Transgenic Maize Plants by Tissue Electroporation."

Fang, R. et al. (Jan. 1989), *The Plant Cell*, 1:141–150 "Multiple cis Regulatory Elements for Maximal Expression of the Cauliflower Mosaic Virus 35S Promoter in Transgenic Plants."

Gubler, F. et al. (Nov. 1992), *The Plant Cell*, 4:1435–1441 "Gibberellin–Responsive Elements in the Promoter of a Barley High–pI α–Amylase Gene."

Hiei, Y. et al. (1994), *The Plant Journal*, 6(2):271–282 "Efficient transformation of rice (*Oryza sativa* L.) mediated by *Agrobacterium* and sequence analysis of the boundaries of the T–DNA."

Horsch, R.B. et al. (Mar. 8, 1995), *Biological Sciences, Monsanto Company*, pp. 1229–1231 "A Simple and General Method for Transferring Genes into Plants."

Ishida, Y. et al. (Jun. 1996), *Nature Biotechnology*, 14:745–750 "High efficiency transformation of maize (*Zea mays* L.) mediated by *Agrobacterium tumefaciens*."

Jensen, L. G. et al. (1998), *Hereditas*, 129:215–225 "Inheritance of a codon–optimized transgene expressing heat stable (1,3–1,4)–β–glucanase in scutellum and aleurone of germinating barley."

Jensen, L. G. et al. (Apr. 1996), *Proc. Natl. Acad. Sci. USA*, 93:3487–3491 "Transgenic barley expressing a protein–engineered, thermostable (1,3–1,4)–β–glucanase during germination."

Kadziola, A. et al. (1994), *J. Mol. Biol.*, 239:104–121 "Crystal and Molecular Structure of Barley α–Amylase."

Kondo, H. et al. (1989), *Gene*, 81:259–265 "Cloning and sequence analysis of the genomic DNA fragment encoding oryzacystatin."

Laursen, C. M. et al. (1994), *Plant Molecular Biology*, 24:51–61 "Production of fertile transgenic maize by electroporation of suspension culture cells."

Leah, R. et al. (1991), *The Journal of Biological Chemistry* 266(3):1564–1573 "Biochemical and Molecular Characterization of Three Barley Seed Proteins with Antifungal Properties."

Leah, R. et al. (1994), *The Plant Journal*, 6(4):579–589 "Identification of an enhancer/silencer sequence directing the aleurone–specific expression of a barley chitinase gene."

Liu, Y. et al. (1995), *The Plant Journal*, 8(3):457–463 "Efficient isolation and mapping of *Arabidopsis thaliana* T–DNA insert junctions by thermal asymmetric interlaced PCR."

MacGregor, A. W. et al. (Jul.–Aug. 1987), *J. Inst. Brew.* 93:334–337 "Studies on β–Glucosidase in Barley and Malt."

McCormac, A.C. et al. (1998), *Euphytica*, 99:17–25 "The use of visual marker genes as cell–specific reporters of *Agrobacterium*–mediated T–DNA delivery to wheat (*Triticum aestivum* L.) and barley (*Hordeum vulgare* L.)."

(List continued on next page.)

Primary Examiner—Phuong T. Bui
(74) Attorney, Agent, or Firm—Merchant & Gould P.C.

(57) ABSTRACT

Tissue-specific regulatory sequences, including promoters from barley (*Hordeum vulgare*) genes encoding α-glucosidase and cystatin-1 (cysteine protease inhibitor) have been identified and isolated. The gene promoters have particular utility in directing high level, germination preferred expression of heterologous proteins that impart increased agronomic and malting characteristics to a given plant. In addition, the invention relates to methods of producing transgenic plants by using chimeric genes, cassette vectors, kits, cells and methods comprising the promoter and signal sequence coding region of the gene for barley α-glucosidase and the gene for barley cystatin-1.

19 Claims, 15 Drawing Sheets

OTHER PUBLICATIONS

Mikkonen, A. et al. (1996), *Plant Molecular Biology*, 31:239–254 "A major cystein proteinase, EPB, in germinating barley seeds: structure to two introless genes and regulation of expression."

Monroe, J. D. et al., (1997), *Plant Physiol,* 115 p. 863 with attached sheets 1 and 2 "The Electronic Plant Gene Register," Plant Gene Register PGR 97–141, Nucleotide Sequence of an β–Glucosidase Gene (Accession No. AF014806) from *Arabidopsis thaliana*.

Morelli, G. et al. (May 1985), *Nature*, 315:200–204 "A short conserved sequence is involved in the light–inducibility of a gene encoding ribulose 1,5–bisphosphate carboxylase small subunit of pea."

Nielsen, H. et al. (1997), *Protein Engineering*, 10(1):1–6 "Identification of prokaryotic and eukaryotic signal peptides and prediction of their cleavage sites."

Olsen, O. et al. (1989), *Carlsberg Res. Commun.,* 54:29–39 "Procession and Secretion of Barley (1–3, 1–4)–β–Glucanase in Yeast."

Politz, O. et al. (1993), *Eur. J. Biochem.,* 216:829–834 "Determinants for the enhanced therostability of hybrid (1–3,1–4)–β–glucanases."

Skriver, K. et al. (Aug. 1991), *Proc. Natl. Acad. Sci. USA*, 88:7266–7270 "Cis–acting DNA elements responsive to gibberellin and its antagoist abscisic acid."

Southern, E. M. (1975), *Mol. Biol.,* 98:503–517 "Detection of Specific Sequences Among DNA Fragments Separated by Gel Electrophoresis."

Sugimoto, M. et al. (1997), *Plant Molecular Biology*, 33:765–768 "Molecular cloning and characterization of a cDNA encoding β–glucosidase from spinach."

Taylor, M. A. et al. (1998), *The Plant Journal*, 13(3):419–425 "cDNA closing and characterisation of an α–glucosidase gene from potato (*Solanum tuberosum* L.)."

Tibbot, B. K. et al. (1996), *Plant Molecular Biology*, 30:229–241 "Molecular cloning and characterization of a gibberellin–inducible, putative α–glucosidase gene from barley."

Tingay, S. et al. (1997), *The Plant Journal*, 11(6):1369–1376 "*Agrobacterium tumefaciens*–mediated barley transformation."

von Heinje, G. (1986), *Nucleic Acids Research*, 14(11):4683–4690 "A new method for predicting signal sequence cleavage sites."

Waldron, C. et al. (1993), *Plant Molecular Biology*, 23:801–812 "Characterization of a genomic sequence coding for potato multicystatin, an eight–domain cystein proteinase inhibitor."

Wan, Y. et al. (1994), *Plant Physiol.,* 104:37–48 "Generation of Large Numbers of Independently Transformed Fertile Barley Plants."

Wolf, N. (1992), *Mol. Gen. Genet.,* 234:33–42 "Structure of the genes encoding *Hordeum vulgare* (1–3,1–4)–β–glucanase isoenzymes I and II and functional analysis of their promoters in barley aleurone protoplasts."

FIG. 2A

*SacI*

| | | | | | | |
|---|---|---|---|---|---|---|
| GAGCTCATGG | TTTTAAACTG | AGATGAATTT | TAATTTTGGG | TGGTGTGATT | TTCCTGTCAA | 60 |
| TGTCACAACA | CAGATTTTCG | TATCTTCCAT | GCTAAACACA | TTATTGGCCA | TTCCCAAACA | 120 |
| TAAATATAAA | GTTTACTCCC | ATCCATCATT | CATACACAAG | CCATGGCTGA | CCATCCTCGG | 180 |
| ATGTCCCCCA | ACATTTCAAC | TGTTCCGCAA | GTTTTGTTTA | ATTATTTTTT | ATTATGCTGG | 240 |
| AGTGAGCATT | CTTTTTACGA | GCCTCTCTTG | TGCAATGAAA | AATGGTGTAC | TGATGTTCCG | 300 |
| CAAAAAATGA | AAGTAATAGC | TTGGAAAGCT | TCAGCGCGCA | CTATCTACAA | TGCTAGGTAA | 360 |
| GGTGGAGCAT | CATATTGGTG | TTCGTGCTAC | ATGTGTGATC | TGTGGTATGG | AGGATGGATC | 420 |
| AAGTTTTCAT | ATGCTCGTTA | CTTGTTATCA | TGCACACGAG | CTTTGGGAGC | GTATGCGGGA | 480 |
| GGTTTGGCCT | CTCCCTCCGC | TAGAGCGACT | ACAACATTCA | GAGAAGGATT | GGCTTCTTTT | 540 |
| ATTATTGGAT | GGTTGTTCGG | CAACTACTAG | AAGCATGATT | ATTTGTTAG | TGTGGAGAAT | 600 |
| CTGGAATTTA | AGGAATGATA | TAGTCCATGA | TAAGGATGCT | ACTCCCACAT | ACGTTTCGTT | 660 |
| TGAATTTTTC | CAAAGTTATC | GACGGTCCCT | TGATAACGAT | CAAATACTCG | TCTGAGGAGA | 720 |
| TACCAAAGGG | AAAGATGCCT | TGATCAGTA | CTAATAACGC | GTTCATTGTG | CCGGTTTCGA | 780 |
| AACTAGCCTT | ATGTTGGACA | CCACCACCAC | AGGGACAGTC | TGCATTATCA | TTTGATGGTT | 840 |
| CCTTCTCGAC | TGCAAATAGT | ACCGCGGCGA | CATGTATGAT | CTTAAGGAGG | TATGATGTAG | 900 |

FIG. 2B

```
                                                          XhoI
TGTTATTTTT GCGGCATACA TATTCTTATT TCATTGCAAT GATGCACTCG AGGCTGAGAT    960

CCACACGATA ATGCAAGATA TGGCTGTTGC AATTCAACAT ACGGATCTAC GTTCAATTTG   1020

ACTCGTCCAT GGCTCTATCT ACACTTGTTG ATGACTACGT TGACCGTTCT GCATACGCTC   1080

ATTTGACTTT GAAGATTAAA GCACTTGTGG TTGATATGGA GTTTGTTCCA TCAAAATTAC   1140

ATCGTGTTCA AAATAGAGTA GCAGATTGTT TGATAAGGTA TAGTCGTTCT AAGTGTACTA   1200

CATATGTGTG GTTACACAAA TGGTCTCATT TATCAAGGAA ATTTTACCTC TAGACTGTAA   1260

CTCTATTACT TTGAAATAAA ACTCCTTATT TTGTTGGGAA AAAAATACGG TTGTAGAGGT   1320

TCGGTTAGAA ATGCCAGATC TATGAATGCA CTAGGACTCA TCGCAAGGTT ACGTGCACGT   1380

CGAGTCAGAG AAAATGTGTG GCCTTTGAAA AATCCATGCT GCCGTATACG CTCGAAATAC   1440

GCACCTGCCT AGTATACTAC GTAGTATATC TTACACGGAC GATTGATTGA ATGAACGAAC   1500
               GARE
GAATTAAGAA ACGCACGCAG CGAGGAGGGC GGGCCGGTCA GCGGGAGTCT GCGTACGTGC   1560

TCACCCCGCC CGTAGACCAC TCGCCGCTCG CCACCGTTGC GGCAAGTAAC AGCCCACTGG   1620

GTCTTATCGC CGGCACCGGT CCCGATGCGT CGACCGCAGC CGCCGCCGAC GGCTCTGGAA   1680

GGAAGGAAGA CCCGTACCGC GCCATGCCGT TACCCCTGGG CGCGCGGTGC CGGGCAACGG   1740
                                                         CAAT box
CCGGATTCCA TGATCTGCTC GCGTCTCCCC CATGCCATGC CGTGATACCG AACCAACCGG   1800
                                                     TATA box
CCAACCAAAG CGGCCACGAT TGGTCCATTT GGACGGCCGG CGATCCTATA AGTACAGGTG   1860

CCATCGCTCG CCGATCGACA CAGCGACAAG CGCAAGACCG TCACACACAC ACACACACCA   1920

GCCCCATCCGATGGCGACGCGGTCGCTGCTGCTGCTCTGCTTGTGTCTCTGCTTATTCGCGCCCC  1980
            M  A  T  R  S  L  L  L  L  C  L  C  L  C  L  F  A  P    18

GCCTGTGCTCGTCC                                                      1994
 R  L  C  S  S                                   23
```

Barley α-glucosidase

Barley high-pI α-amylase

FIG. 4

| Plasmid | Promoter | Signal peptide | Gene for H(A12-M)ΔY13 | Restriction map |
|---|---|---|---|---|
| pCT1 | Barley high-pI α-amylase | Barley high-pI α-amylase | Synthetic; high G-C content | BamHI, SacI — α-AMY — SfiI — ΔY13-GC — SacI, EcoRI — nos |
| pCT2 | Barley high-pI α-amylase | Barley high-pI α-amylase | Non-modified; low G-C content | BamHI, SacI — α-AMY — SfiI — ΔY13 — SacI, EcoRI — nos |
| pCT3 | Barley α-glucosidase | Barley high-pI α-amylase | Synthetic; high G-C content | XhoI — α-GLU — SfiI — ΔY13-GC — SacI, EcoRI — nos |
| pCT4 | Barley α-glucosidase | Barley α-glucosidase | Synthetic; high G-C content | XhoI — α-GLU — XhoI — ΔY13-GC — SacI, EcoRI — nos |

| Plasmid | Promoter | Signal peptide | Restriction map |
|---|---|---|---|
| pCT5 | Barley high-pI α-amylase | None | HindIII, SacI — α-AMY — BamHI — GUS — SacI, EcoRI — rbc |
| pCT6 | Barley α-glucosidase | None | HindIII — α-GLU — BamHI — GUS — SacI, EcoRI — rbc |

FIG. 7

```
        Primer D
●─────────────▶
ATGGAGATGTGGAAATATCGGGTCCTGGGATCGGTTGCTGCCCTGCTCTTGCTGCTCGCC          1568
 M  E  M  W  K  Y  R  V  L  G  S  V  A  A  L  L  L  L  L  A            20

GTCGTCGTGCCGTTTACTCAGACCTGGACGCAGAGCGCGCGGGACAAGGCTGCCATGGCG          1628
 V  V  V  P  F  T  Q  T▲ W  T  Q  S  A  R  D  K  A  A  M  A            40
                       ↑
                                        Primer C
                                  ◀───────────────●
GAAGACGCGGGGCCGTTGATGGGAGGCATCGAGGACTCGCCGATGGGACAAGAGAACGAC          1688
 E  D  A  G  P  L  M  G  G  I  E  D  S  P  M  G  Q  E  N  D            60
                                       Primer B
                                  ◀───────────●    ◀─────────
CTCGACGTCATCGCGCTCGCCCGCTTCGCCGTCTCCGAGCACAACAAGAAGGCCAATGCC          1748
 L  D  V  I  A  L  A  R  F  A  V  S  E  H  N  K  K  A  N  A            80

Primer A
─────────────────●
CTGCTGGAGTTCGAGAATGTGGTGAAGCTGAAGAAACAAACTGTTGCTGGCACCATGTAC          1808
 L  L  E  F  E  N  V  V  K  L  K  K  Q  T  V  A  G  T  M  Y           100

TACATTACAATTCGGGTCACTGAAGGTGGGACCAAGAAGCTCTATGAAGCTAAGGTGTGG          1868
 Y  I  T  I  R  V  T  E  G  G  T  K  K  L  Y  E  A  K  V  W           120

◀─────────────────
GAGAAACTATGGGAGAACTTTAAGCAGCTTGAGGAGTTCAAGCCGGTGCAGGACGCTGCA          1928
 E  K  L  W  E  N  F  K  Q  L  E  E  F  K  P  V  Q  D  A  A           140

Primer E
───────────●
ATTGCATAA                                                             1937
 I  A                                                                  142
```

FIG. 8A

```
        Primer AD3
      ●────────────▶
      AGTGGAGAAG CATAGGGACA ATATTTACCC AGGTTCGGGC CCTCTCGAAG AGGTAAAACC      60

CTACGTCCTC CTTGATTATA TTGTTGTGTG TATGACGATT ATATAGTCGA TCTACCGCGA     120

GATCATATGA ACTAAGCCCT AGATGAGTAG GATAATGGTT CTCCCCTCTA CAATCTAAAC     180

CCTCTGAGTT ATATAGACAT CAGGGGTACC TAGGGTTATA CTGGGAGGTT GCCATCAAGG     240

AATAGACATG TCGATTCTAC CATCTTGACT TGGGAGGACA CACCAAGGCT TACAGATTTC     300

CTTCGTGAAC GCGTAGTTAT GTTATAGCTC GGCCTTCCAC AAAGCGGCCC ACCTGTCCAT     360

CCCACAAGTG ATAGACCGGC AGTCTGATGA TCCCTTAGTC CCGGACTCCC TTACCACTCG     420

CTGATGGTTG TTGTCAGCCA GATCTTCTCG CCTCATATGC TCCCCATAGG TATTGTCGCC     480

GCCAATGCTC GCATATTTGA GAGAGTGATA GTGAAGAAAT ATGAAAATGA ACGGTGAAGG     540

GATTTTTGGC CCGCCCTTGG GAAAAAACGC ACAGTTCCTC GCTTGTCCCC ACACGTGCAA     600

CCCCGTGGCC TAGATGTTCC TACTCACGTC TGACTTCCTG GAAATGTTCG ATCGGTCGTT     660

CCTCCAAACT CAAACTCTGA GCTGCTTTAA TAAATCCAGC CGCACACGTG TACTTCCTCC     720

GTCTCAAAAT AAGTAGCTTA TTACAATTTT ATACTAAAAC TATTACAAAG TTGAGATAGT     780
```

FIG. 8B

```
TATTTTAAAA TGGAGGAAGT AGGTAACAAA GTGGGACAAA TTTGATCCCC ACGGAATTCC    840

TTTATCTTTG CAAATCCAAG CAATCTAATG GATTTTCTAG GGTCAAGCAT GAGTGTGAAT    900

TAAGGATCAA GCAAAACTTC TGGACAGATA AGCATCAACT TGTCAGTTGT CACAGATACA    960

CGCATGCGTA ATGAGTCATA TACATATACA TACGTGGCAA AATTTCGCCC TCGTCACTTC   1020

ATTACGACTT ATAATCTTGA CTTAAACCCA AGAATTCGCA CCCAGTTTTT TCATTTCAGC   1080

AAGGCGTTTT GCTTCCATTT GTTATCCCAG CTTTGCTCCT CTGTCATCCA TGGATCCACC   1140

CATATAGGAA GATAGAAAAG GATAATCCCC TTATTGTTCT TTGTTGACTT TGCATGAACA   1200

AGGAAATCAG AAGATAAACA TCTAGCCTAG GGAGAAGGAA GGAATCCAGC CGAGACCCAC   1260

AGTGTCGCCA TTGGCGACAG CATAGCGTGT AACCTAAGCT GTAAACCCCT CGGGATTGGG   1320

GAAAAGGGCC GTGGTAGGAC CCAACGATGC GGGGCCCGTC CATTCTATTC CGTCCGTTCC   1380
                                                CAAT box
CGTGTCCCGT CCAGACTCAG AGTGTCCCCA CACAATAATT TCGCCGACGG ATCGTACTCC   1440
                                                       TATA box
TACCCTTCTC CCCCCAATAC CGGGCCTGCT CTGCTACTGC AGCTATAAAT CCCGACCCCG   1500

ATAGGTCG                                                             1508
```

FIG. 8C

```
                    Primer D
            ●━━━━━━━━━━━━━━▶
            ATGGAGATGTGGAAATATCGGGTCCTGGGATCGGTTGCTGCCCTGCTCTTGCTGCTCGCC              1568
             M  E  M  W  K  Y  R  V  L  G  S  V  A  A  L  L  L  L  A                 20

GTCGTCGTGCCGTTTACTCAGACCTGGACGCAGAGCGCGCGGGACAAGGCTGCCATGGCG              1628
             V  V  V  P  F  T  Q  T  W  T  Q  S  A  R  D  K  A  A  M  A               40
                                    ↑              Primer C
                                                ◀━━━━━━━━━━━━━●
            GAAGACGCGGGGCCGTTGATGGGAGGCATCGAGGACTCGCCGATGGGACAAGAGAACGAC              1688
             E  D  A  G  P  L  M  G  G  I  E  D  S  P  M  G  Q  E  N  D               60

CTCGACGTCATCGCGCTCGCCCGCTTCGCCGTCTCCGAGCACAACAAGAAGGCC                    1742
             L  D  V  I  A  L  A  R  F  A  V  S  E  H  N  K  K  A                      78 gtaagccctcgctatcccctctctctctctctcatgtccatccctgcgagtgaggtcca              1802 actggatctgagttcgacggccgggctgttggatccacagagctttggtcactggccctt              1862 ctgtagtattacatcgacgatcgatctaagttaaagtcaaccgccgtaaatcatacagta              1922 tgaatcttcgcgattttgatttaagccatggcgcctttttctcaacaaaaagaacac                 1982 ctgaagtatatttgacaggcagcccaacagcaagtgctcctgctagatttgccggattat              2042 tatttgttctaagtattatccaatactagtaagttccccatgacaatggaggtttgttag              2102 ttggattgattttttttggcgctaccctgtcacag                                        2138

AATGCCCTGCTGGAGTTCGAGAATGTGGTGAAGCTGAAGAAACAAACTGTTGCTGGCACC              2198
             N  A  L  L  E  F  E  N  V  V  K  L  K  K  Q  T  V  A  G  T               98

ATGTACTACATTACAATTCGGGTCACTGAAGGTGGGACCAAGAAGCTCTATGAAGCTAAG              2258
             M  Y  Y  I  T  I  R  V  T  E  G  G  T  K  K  L  Y  E  A  K               118
                                                            ◀━━━━━━━━━━━
            GTGTGGGAGAAACTATGGGAGAACTTTAAGCAGCTTGAGGAGTTCAAGCCGGTGCAGGAC              2318
             V  W  E  K  L  W  E  N  F  K  Q  L  E  E  F  K  P  V  Q  D               138
                    Primer E
            ━━━━━━━━━━━━●
            GCTGCAATTGCATAA                                                            2333
             A  A  I  A                                                                 142
```

Barley cystatin

MEMWKYRVLGSVAALLLLLAVVVPFTQTWTQSARDKAAMAEDAGPLMGGI

Barley high-pI α-amylase

MANKHLSLSLFLVLLGLSASLASGQVLFQGFNWESWKHNGGWYNFLMGKV

GERMINATION-SPECIFIC PLANT PROMOTERS

FIELD OF THE INVENTION

The invention relates to regulatory sequences directing tissue-specific expression of a heterologous gene in a plant, and more particularly to DNA promoter sequence capable of conferring germination-specific expression of a gene in plant tissue.

BACKGROUND OF THE INVENTION

An important goal of plant biotechnology is to genetically engineer plants so they have a new or improved trait or characteristic. Initially, transformation was developed in model dicot plants. Monocot plants, which include all the major cereal crops, were more difficult, and the first successful transformations, in rice and maize, were not reported until the late 1980s. Although consistent transformation of the more recalcitrant cereals such as wheat and barley have only been achieved very recently, it has been shown that a homozygous transgenic barley line can transmit a heterologous gene over three generations to all progeny plants (Jensen et al., 1998, *Hereditas* 129:215–225).

While tissue-specific, heterologous gene expression in plants can be achieved, the current stage of genetic engineering methodology does not offer the means of targeting where introduced DNA sequences are integrated into the chromosome; integration into plant chromosomes appears to be more or less random.

This invention relates to transgenic plants and involves a method of generating transgenic plants with controllable gene expression. Particularly, the invention relates to transgenic plants that have been modified such that expression of a heterologous introduced gene can be limited to a particular stage of plant development, a particular plant tissue, particular environmental conditions, or a particular time or location, or a combination of these situations. More particularly, attention has been given to produce transgenic cereal plants of the grass family; common cereal plants include barley (Hordeum), wheat (Triticum), rice (Oryza), maize (Zea), rye (Secale) and sorghum (Sorghum).

A desired trait or characteristic is introduced into the plant by incorporating into the plant's genome a gene that encodes the polypeptide that confers the desired trait or characteristic. DNA sequences that regulate the expression of the gene must also be introduced into the plant in conjunction with the desired gene. For heterologous expression, the regulatory sequence—such as a sequence often called a gene promoter, or simply a promoter—directs transcription of a large number of RNA molecules from the operably linked heterologous DNA sequence, which serves as a template. Each plant gene comprises a promoter sequence to which specialized proteins bind and activate the gene. For example, specific nucleotide sequences within the promoter are recognized by RNA polymerase molecules that start RNA synthesis. After primary transcription, a second class of signals leads to the termination of RNA synthesis and the detachment of RNA polymerase molecules from their respective DNA templates. The RNA chains, which may undergo further processing, e.g. removal of intron sequences and attachment of poly(A) tails, can in turn serve as templates for the synthesis of specific polypeptide chains.

The selection of a promoter is often a critical factor in obtaining expression of a heterologous gene. A promoter can function as a constitutive promoter or as an inducible promoter. Constitutive promoters are those which are capable of expressing operably linked DNA sequences in all tissues of a plant throughout development. Even though providing constitutive expression of a gene in plants is often desirable, it is also desirable in some instances to direct expression of a gene to particular tissues and/or time of development in a plant. Tissue specific promoters are capable of selectively expressing heterologous DNA sequences in certain plant tissues. Tissue specific promoters may also be inducible, e.g. activated by application of external or internal inducing agent, such as gibberellic acid and abscisic acid which are known to exercise important control at the transcriptional level over a-amylase gene expression in aleurone cells (Skriver et al., 1991, *Proc. Natl. Acad. Sci. USA* 88:7266–7270; Gubler and Jacobsen, 1992, *Plant Cell* 4:1435–1441).

Of particular interest to the present invention are tissue specific promoters. These promoters can be fused with a heterologous DNA sequence and used to transform a plant cell to create a transgenic plant that selectively expresses the heterologous DNA in a specific tissue. Several promoters are currently being used for tissue-specific, heterologous gene expression in monocot cells. For example, the promoter regions from genes coding for hydrolases have been used to direct germination-specific expression of a heterologous DNA sequence in transgenic monocot cells (see Skriver et al., 1991, supra); Wolf, 1992, *Mol. Gen. Genet.* 234:33–42; Mikkonen et al., 1996, *Plant Mol. Biol.* 31:239–254; Jensen et al., 1996, *Proc. Natl. Acad. Sci. USA* 93:3487–3491; Jensen et al., 1998, supra; U.S. Pat. No. 5,712,112).

A variety of plant promoters with different characteristics and which are effective in different plant species and/or organs is desirable in order to bring potential applications of transgenic plants into practice. Since the task of successfully cloning and demonstrating the utility of a highly expressed promoter is formidable, the use of systems for transient expression of heterologous genes in protoplasts has proven ideal to predict whether a gene construct will function during plant germination (Jensen et al., 1996, supra).

Since the location of the heterologous gene in the host's DNA can affect the efficiency with which it is expressed, it is often necessary to produce many individual transgenic plants to ensure that an effective line with the desired characteristics can be selected from them. These plants are then bred conventionally.

In view of the widespread occurrence of α-glucosidases in higher plants and their potential importance in carbohydrate metabolism, it is surprising that there are only a few reports on α-glucosidase genes. These include cDNA sequences for α-glucosidases of barley (Tibbot and Skadsen, 1996, *Plant Mol. Biol.* 30:229–241), spinach (Sugimoto et al., 1997, *Plant Mol. Biol.* 33:765–768), and potato (Taylor et al., 1998, *Plant J.* 13:419–425), as well as a genomic sequence of an α-glucosidase gene from *Arabidopsis thaliana* (Monroe et al., 1997, *Plant Physiol.* 115:863; GenBank Accession No. AF014806).

Only a few genomic DNA sequences encoding plant cystatins have been described, including the genomic sequence for rice cystatin (Kondo et al., 1989, *Gene* 81:259–265), the sequence for potato cystatin (Waldron et al., 1993, *Plant Mol. Biol.* 23:801–812), and the sequence for maize cystatin (Abe et al., 1996, *Biosci. Biotech. Biochem.* 60:1173–1175).

In no previously reported case has an α-glucosidase gene promoter or a cystatin gene promoter been used to direct heterologous expression in plants. One object of the present invention is therefore to provide an α-glucosidase gene promoter or a cystatin gene promoter from an industrially important organism, and utilize the promoter to direct expression of heterologous protein in monocotyledonous grass plants, including the cereals.

SUMMARY OF THE INVENTION

Novel germination-specific promoters have now been identified and isolated from the barley genome. Two such useful regulatory sequences described and claimed herein are the promoters of the α-glucosidase gene and the cystatin-1 genes from barley, which are useful to express a desired heterologous gene at high levels in the aleurone tissue of germinating kernels, particularly barley. In a preferred embodiment, these promoters are used to induce expression of heterologous genes in the aleurone tissue of kernels during germination, including the process of malting, for example, in the production of a brewed product such as beer.

An isolated nucleotide sequence comprising at least 1930 base pairs (hereafter abbreviated bp) upstream of the translational start site of the sequence encoding the α-glucosidase gene was found to be a useful tissue specific promoter (FIG. 2), [SEQ ID NO:1]. A useful promoter fragment of 984 bp in length was isolated (FIG. 2), [SEQ ID NO:2] and used to direct tissue-specific expression of a heterologous gene in monocotyledonous plant cells and plant tissues.

An isolated cDNA sequence encoding barley cystatin-1 was cloned and characterized (FIG. 7) [SEQ ID NO: 5]. Moreover, the gene promoter and protein coding region was cloned (FIG. 8), [SEQ ID NO: 15]. This sequence includes 1508 bp upstream of the translational start site, which was found to be a useful tissue specific gene promoter [SEQ ID NO: 14]. The accumulation of cystatin-1 mRNA transcripts in barley kernel during germination is particularly enhanced under malting conditions.

The present invention provides nucleic acid sequences defining the α-gluocosidase gene promoter region [SEQ ID NOS: 1 and 2], and the cystatin-1 gene promoter region [SEQ ID NO: 14].

The invention also includes a chimeric gene comprised of the α-glucosidase gene promoter or the cystatin gene promoter operably linked to a DNA sequence comprising an open reading frame that is heterologous to the gene promoter. Preferably, the protein coding region of the gene is also operably linked to a 3' non-translated polyadenylation region. The invention further includes transformed plant cells and plant tissues comprising this chimeric gene; and transgenic plants comprising a gene sequence which expression is regulated by an α-glucosidase gene promoter or a cystatin gene promoter, where said gene sequence is heterologous to the gene promoter. In a further embodiment, the present invention is directed to a recombinant vector, preferably a plasmid, comprising the recombinant DNA molecules described above.

Such recombinant DNA molecules, or vectors containing the DNA molecules, are introduced into plant cells so that the gene promoter preferentially directs expression of the heterologous gene in aleurone cells. Having disclosed the barley α-glucosidase gene promoter and cystatin-1 gene promoter sequences and their ability to direct germination-specific expression of heterologous genes in a plant, those skilled in the art can readily appreciate the identity of other equivalent nucleotide sequences (i.e. gene promoters) capable of directing expression of similar α-glucosidases and cystatins. Thus, the scope of the subject invention includes not only the specific nucleotide sequences disclosed herein, but also structurally and functionally equivalent nucleotide sequences directing expression of molecules with the same α-glucosidase or cystatin activity. These equivalent molecules can be identified, for example, by cross-hybridization to parts of the barley α-glucosidase gene promoter sequence [SEQ ID NO:1] as shown in FIG. 1B, or the cystatin-1 promoter sequence [SEQ ID NO: 14] under conditions of stringency as is well understood in the art and described, for example, in Sambrook et al., Molecular Cloning: A Laboratory Manual (New York: Cold Spring Harbor Laboratory Press, 1989).

The invention further comprises methods for generating a transgenic plant by introducing a chimeric gene, preferably together with a selectable marker gene, into plant cells, plant tissue and plants where the chimeric gene is comprised of an α-glucosidase gene promoter or a cystatin-1 gene promoter, a gene sequence which is heterologous with respect to the promoter, and preferably a 3' non-translated polyadenylation region. Plant cells are cultured in a growth medium preferably containing a selection agent to identify those plant cells with the chimeric gene. The transformed plant cells are then regenerated into whole plants.

The present invention provides transformed plant cells, plant tissues, and transgenic plants expressing heterologous proteins as directed by an α-glucosidase gene promoter or a cystatin-1 gene promoter.

The invention further includes transformed plant cells and tissues, and transgenic plants expressing heterologous proteins that are targeted for secretion by use of an α-glucosidase signal sequence, e.g., barley α-glucosidase signal sequence [SEQ ID NO:4], or by use of a cystatin signal sequence, e.g. barley cystatin-1 signal sequence [SEQ ID NO:8]. Thus, the present invention can be used to secrete heterologous proteins from kernel cells and tissues, e.g. barley kernel cells and tissues. Specifically, the functioning of the heterologous constructs as described in the Examples below proves that the signal peptide of barley α-glucosidase can be used to confer secretion of heterologous proteins from barley cells to the extracellular space.

Controlling the expression of genes that direct expression of heterologous proteins has particular utility in industrial applications, such as malting of cereals. Accordingly, the present invention is particularly useful in the brewing industry.

BRIEF DESCRIPTION OF THE DRAWINGS

FIG. 1A is a restriction site map of a 9.8-kbp fragment of barley genomic DNA inserted into a Lambda phage. A thin line indicates phage DNA; a thick line indicates barley DNA; a black box indicates the SacI-NotI fragment which contains the barley α-glucosidase promoter and a short sequence of the protein coding region, including the ATG translational start codon; a dotted line indicates the fragment used as probe in the blot shown in FIG. 1B. The gene promoter fragment from the SacI site downstream to the translational start codon represents 1930 bp. A horizontal arrow indicates the position of the sequence shown in FIG. 2. The length of the arrow corresponds to 1994 bp.

FIG. 1B is a Southern blot of genomic DNA from the barley (lanes 2–4), wheat (lanes 5–7), rice (lanes 8–10), maize (lanes 11–13), rye (lanes 14–16) and sorghum (lanes 17–19) digested with BamHI (B), XhoI (X) and HindIII (H). Lane 1 contains marker DNA (Life Technologies; Cat. No. 15615-016), with lengths (in bp) of selected fragments indicated to the left. The DNAs on the filter were hybridized with a $^{32}$P-labelled fragment of the barley α-glucosidase cDNA gene corresponding to nucleotides 385–2725 of plasmid pAGL.2752 (Tibbot and Skadsen, 1996 supra; GenBank Accession No. U22450).

FIGS. 2A–2B shows the DNA sequence of the promoter for the gene encoding barley α-glucosidase as illustrated in FIG. 1A. The nucleotides are numbered as indicated to the right of the sequence. The SacI site located at nucleotides 1 to 6, marked with "SacI", corresponds to the SacI site at the 5' end of the gene promoter illustrated in FIG. 1A. The XhoI restriction site located from nucleotides 947–952, used for construction of expression plasmids, is marked with "XhoI". A putative gibberellin response element, similar to those identified by Skriver et al. (1991, supra) is located from nucleotide 1505 to 1513, and marked with "GARE". A putative CAAT box, located at nucleotide 1793 to 1797, is marked with "CAAT". The putative TATA box is an eight-bp sequence, marked with "TATA", and located from nucleotides 1847 to 1854. The nucleotide "G" marked at position 960 corresponds to the 5' base of cDNA clone pAGL.2752 (GenBank accession No. U22450). The translational start codon ATG, marked in bold type, is located from nucleotides 1931 to 1933. The signal peptide coding region from nucleotide 1931 to 1994 is listed above the deduced protein sequence, with corresponding amino acid residues shown in the standard one letter code. A vertical arrow indicates the predicted site of signal peptidase cleavage (see FIG. 3).

FIG. 4 presents a survey of the plasmid constructs used for transfection of barley aleurone protoplasts. On the schematic restriction maps, not drawn to scale, are indicated, from left to right: the gene promoter (large open box), 5' non-translated sequence between transcription start site and translational start site (small open box), DNA sequence encoding signal peptide (dotted box), sequence for H(A12-M)ΔY13 or β-glucuronidase (thick box), and terminator sequence (box with diagonal lines). The restriction site positions are indicated. Abbreviations: α-AMY: barley high-pI α-amylase gene promoter; ΔY13: non-modified sequence encoding heat stable (1-3,1-4)-β-glucanase H(A12-M)ΔY13; ΔY13-GC: synthetic sequence encoding heat stable (1-3,1-4)-β-glucanase H(A12-M)ΔY13; nos: *Agrobacterium tumefaciens* nopaline synthase gene terminator; rbc: terminator sequence of the pea gene encoding ribulose 1,5-bisphosphate carboxylase.

FIG. 7 illustrates the protein coding region of the cDNA sequence for barley cystatin-1. The derived protein sequence is shown below the DNA sequence. Oligonucleotide primers in sense and antisense orientation which were used to amplify the gene sequence are indicated with horizontal arrows in left-to-right and right-to-left orientation, respectively. Filled circles and arrowhead ends illustrate oligonucleotide 5' and 3' ends, respectively. A vertical arrow indicates the predicted site of signal peptidase cleavage (see FIG. 10).

FIGS. 8A–8C detail the nucleotide sequence of the barley cystatin-1 gene, where the nucleotides are numbered as indicated to the left of the sequence. The CAAT box and TATA box are located at nucleotide positions 1413–1416 and 1484–1490, respectively. The gene segment between the translation start codon ATG (nucleotide 1509 to 1511) and the translational stop codon TAA (nucleotide 2331 to 2333) encodes a cystatin protein with a deduced amino acid sequence of 142 residues, which is given below the nucleotide sequence. A 396-nucleotide long intron sequence which interrupts the protein coding region is shown in lower case letters. Oligonucleotide primers in sense and antisense orientation which were used to amplify the gene sequence are indicated with horizontal arrows in left-to-right and right-to-left orientation, respectively. Filled circles and arrowhead ends illustrate oligonucleotide 5' and 3' ends, respectively. A vertical arrow indicates the predicted site of signal peptidase cleavage (see FIG. 10).

Figure 1A:
FIGS. 1A–1B detail aspects of cereal α-glucosidase gene promoters.

Protoplast aliquots were incubated in the absence (indicated with "-") of phytohormone, or in the presence of either gibberellic acid (indicated with "G") or abscisic acid (indicated with "A"). Details for determination of relative β-glucuronidase activities are given in Example 11.

DETAILED DESCRIPTION OF THE INVENTION

Genetic modification of plants can be used to improve plant characteristics, such as taste, texture, size, disease resistance, and herbicide resistance. Using genetic engineering techniques, it is also possible to introduce traits normally not characteristic of a given plant.

The present invention is directed to the α-glucosidase gene promoters and cystatin promoters capable of directing germination-specific expression, in particular, the barley α-glucosidase gene promoter and cystatin-1 gene promoter described herein. The invention includes vectors, plant cells, plant tissues, and plants transformed with a heterologous gene regulated by these promoters, or fragments thereof.

Definitions

For the purposes of this application, the following terms and phrases have the indicated definitions.

A "gene promoter" refers to a region of DNA upstream from the translational start codon and which acts as a signal for the binding of RNA polymerases to direct expression of the gene, but may also include the 5' non-translated region of the transcript. It is understood that a gene promoter as defined in this application may also include intron sequences that are part of the primary transcript, and which are present in the genomic sequence spanning the region from the transcriptional start site to the translational start site. In general, eukaryotic promoters include a characteristic DNA sequence homologous to the consensus 5'-TATAAT-3' (TATA) box about 10–30 bp 5' to the transcription start site. Another promoter component, the CAAT box, is often found about 30 to 70 bp 5' to the TATA box and has homology to the sequence 5'-CCAAT-3'(Breathnach and Chambon, 1981, *Ann. Rev. Biochem*. 50:349–383). Other sequences conferring regulatory influences on transcription can be found within the promoter region. Promoter function can be tested at the transcriptional stage using DNA-RNA hybridization assays ("Northern" blots) and at the translational stage using specific functional assays for the protein synthesized. Such assays may comprise enzymic activity or by immunoassay of the protein. When a gene promoter directs expression of a protein it is accordingly understood that the transcribed RNA molecules are translated into protein.

An "α-glucosidase gene promoter" according to the invention is a nucleic acid sequence upstream of the coding sequence of the α-glucosidase gene, as shown in FIG. 2 (nucleotides 1–1930) [SEQ ID NO: 1 ]. The α-glucosidase gene promoter of the invention also includes structurally and functionally similar α-glucosidase gene promoters, e.g., portions of the sequence shown in FIG. 2, as well as those derived from other cereal plants, having sufficient sequence homology to hybridize to the barley α-glucosidase promoter sequence of FIG. 2 under standard hybridization conditions, e.g., moderate to high stringency conditions. Cross-hybridization methods for identifying such homologs are described, for example, in Gelvin and Schilperoort (eds.) (1998) *Plant Molecular Biology Manual*, 2nd Edition, Kluwer Academic Publishers, Dordrecht, The Netherlands; Southern, 1977, *J. Mol. Biol*. 98:503–517. One example of such stringency conditions is that used to obtain the result shown in FIG. 1B (1.0×SSC, 0.1% SDS, and 65° C). In addition, one useful promoter sequence is that sequence spanning the region of FIG. 2 between the XhoI site at nucleotide 947 to the start of the coding sequence [Sequence ID no: 2].

A "cystatin-1 gene promoter" according to the invention is the barley cystatin-1 gene promoter having a nucleic acid sequence shown as nucleotides 1–1508 in FIG. 8 [SEQ ID NO:14]. The cystatin-1 gene promoter of the invention also includes structurally similar cystatin-1 gene promoters, e.g., those derived from other cereal plants, having sufficient sequence homology to hybridize to the barley cystatin-1 gene promoter sequence of FIG. 7 under standard hybridization conditions, for example, as described in Gelvin and Schilperoot (eds.), 1998, supra. The abbreviation "cys-1" means the entire gene encoding cystatin-1, that is, the genomic segment spanning sequence from the 5' end of the gene promoter to the 3' end of the transcription termination region. "Standard hybridization" conditions are defined as those parameters which allow discrimination of nucleotide sequences which are structurally similar to a target sequence or which anneal to the target sequence and permit discrimination of the target sequence from non-specific or background nucleic acid with the sequence. Standard hybridization conditions are generally moderate or moderate to high stringency conditions permitting identification of sequences with 80% or more homology, and preferably 90% or more homology, and more preferably 95% or more homology to the target sequence. Percent homology can be determined by one skilled in the art using, for example, sequence alignment analysis. Depending upon the degree of homology desired, hybridization conditions can be determined by a skilled artisan using techniques and computations well known in the art which allow isolation and/or identification of such a sequence.

The term "operably linked" means two structural elements (nucleic acid sequences) linked in a functional manner so as to operate as one unit. For example, a coding sequence and a promoter are to be considered to be operably linked if they are on the same strand of DNA, in the same orientation, and are located relative to one another, such that the promoter directs transcription of the coding sequence.

As used herein, a "heterologous" sequence originates from a foreign source (or species) or if from the same source, is modified from its original form. Thus, any nucleotide sequence material which has been recombinantly introduced into a plant cell, plant tissue or plant host is defined as being heterologous. Similarly, a "heterologous protein" is any protein material which is either heterologous to the selected plant cell, plant tissue or plant host, e.g. are naturally not produced in this host, or natural protein material whose synthesis is directed by genetic information recombinantly introduced into a plant cell, plant tissue or plant.

The term "expression construct" refers to nucleotide sequences which are capable of directing expression of a heterologous gene in hosts compatible with such sequences.

The term "plant" comprises whole plants, plant organs (such as leaves, stems, roots, etc.), kernels, plant cells and progeny of same. It includes plants of a variety of ploidy levels, including polyploid, diploid and haploid.

A "transgenic plant" refers to a plant that has been produced by genetic engineering techniques.

A "cereal" plant as defined in the present invention is a member of the Gramineae plant family cultivated primarily for their starch-containing seeds. Cereal plants include barley (Hordeum), wheat (Triticum), rice (Oryza), maize (Zea), rye (Secale) and sorghum (Sorghum).

A "kernel" is defined to comprise the cereal caryopsis, also denoted internal seed, the lemma and palea. In most barley varieties the lemma and palea adhere to the caryopsis and are a part of the kernel following threshing. However, naked kernel varieties also occur. In these, the caryopsis is free of the lemma and palea and threshes out free as in wheat.

"Malting" is defined as germination under controlled temperature and humidity conditions. Barley for industrial production of beer is normally malted at approximately 15° C. and a relative humidity of 100%.

PROMOTERS OF THE INVENTION

α-Glucosidase Gene Promoter

The promoter region of the α-glucosidase gene from barley was cloned, sequenced, and then introduced into plasmids upstream of DNA sequences encoding protein that is heterologous to barley. The nucleotide sequence of the promoter region [SEQ ID NO:1] is shown in FIG. 2. One active promoter fragment [SEQ ID NO: 2] spans the region upstream of the coding sequence to the XhoI site at about nucleotide 947, shown in FIG. 2.

In the examples below, one series of experiments details directed expression of the heterologous protein, β-glucuronidase, directed by the α-glucosidase promoter fragment. Another series of experiments details directed expression of heat stable (1-3,1-4)-β-glucanase enzyme, which is heterologous to barley, directed by the α-glucosidase promoter fragment [SEQ ID NO:2].

α-Glucosidase is one of several carbohydrases in the germinating barley kernel responsible for the breakdown of starch granules. The action of α-glucosidase on α-glucan polymers and disaccharides liberates glucose. Low amounts of α-glucosidase activity is present in the ungerminated barley grain (MacGregor et al., 1987, *J. Inst. Brew.* 93:334–337), but α-glucosidase activity increases many-fold after the onset of germination of the grain. The increase in α-glucosidase activity during germination of the barley grain is mainly the result of high levels of α-glucosidase gene expression in the aleurone and scutellum tissues of the kernel (Tibbot and Skadsen, 1996, *Plant Mol. Biol.* 30:229–241). Such data enabled Tibbot and Skadsen (1996, supra; U.S. Pat. No. 5,763,252) to obtain a cDNA clone containing the DNA sequence for barley α-glucosidase. Accordingly, the scope of the subject invention includes not only the specific promoter sequence for barley α-glucosidase, but also using this sequence to direct expression of heterologous proteins in barley cells.

The α-glucosidase promoter of barley is highly active in different tissues of germinating barley grains, and can be used to express novel genes in plants, particularly in monocot plants such as barley and other cereal plants.

Cystatin-1 Gene Promoter

Figure 9:
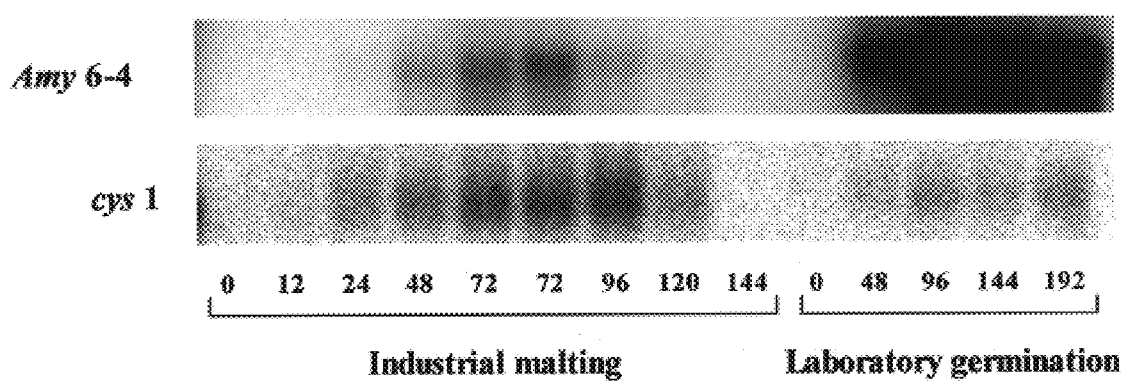
FIG. 9 is a Northern blot of total RNA isolated from barley kernels sampled at regular time intervals after initiation of malting and germination (shown in hours below the blots). The upper blot, indicated with "Amy6-4", was probed with the barley high-pI α-amylase cDNA, clone E , previously described by Rogers and Milliman (1983, *J. Biol. Chem.* 258:8169–8174) and Khursheed and Rogers (1988, *J. Biol. Chem.* 263:18953–18960). Following removal of the α-amylase cDNA probe from the blot, it was rehybridized using the barley cystatin-1 cDNA clone of this invention (indicated with "cys1" in the lower blot).

The promoter and protein coding region of a barley cystatin-1 gene (cys1) has been isolated and sequenced (FIGS. 7 and 8), [SEQ ID NO: 9] and shown to encode a cystatin, based on protein homology to phytocystatins identified in other plants (Brown and Dziegielewska, 1997, *Protein Science* 6:5–12). The barley cys1 gene is expressed in germinating barley grain, primarily in aleurone tissue, as demonstrated by Northern blot analysis of transcript levels in germinating barley grain, detailed in Example 6. In contrast to the barley gene Amy6-4 encoding high-pI α-amylase, the expression of the cys1 gene and accumulation of cystatin-1 mRNA transcripts is greater under industrial malting conditions than under laboratory germination conditions (FIG. 9). The barley cystatin-1 gene promoter residing within nucleotides 1–1508 of FIG. 8 [SEQ ID NO: 14] may be used to direct tissue specific expression of heterologous genes in germinating cereal grain, e.g., in the aleurone tissue of barley kernel, and in particular to direct high levels of gene expression in germinating cereal kernel in an industrial malting plant. Such directed expression is particularly preferred during and immediately following steeping, when the gibberellic acid responsiveness of the kernel is reduced by anaerobic conditions.

Additional Promoters of the Invention

Additional nucleic acid sequences of an α-glucosidase gene promoter or a cystatin-1 gene promoter of the invention may be obtained by screening selected genomic libraries or samples from a source such as a plant cell or plant tissue believed to possess the promoter, using the sequences disclosed herein to design probes. Conventional primer extension procedures as described in the literature can also be used. See, for example, Sambrook et al., supra; Dieffenbach et al., *PCR Primer: A Laboratory Manual*, Cold Spring Harbor Laboratory Press.

The oligonucleotide sequences selected as probes should be of sufficient length and sufficiently unambiguous that false positives or non-specific nucleic acid sequences are minimized. The oligonucleotide is preferably labelled such that it can be detected upon hybridization to DNA in the library or plant sample being screened. Methods of labelling are well known in the art, and include the use of radiolabels such as $^{32}$P-labelled ATP, biotinylation or enzyme labelling. Hybridization conditions, including moderate stringency and high stringency, are provided in Sambrook et al., supra. Depending upon the degree of homology with the target sequence, parameters such as temperature and or salt concentration of hybridization and/or wash conditions can be calculated using known algorithms such as provided, for example in Sambrook et al., supra; or through the NCBI, (URL address http://www.ncbi.nlm.nih.gov/). One skilled in the art will know the appropriate hybridization parameters to use depending upon the particular target sequence.

Sequences identified by such screening methods can be compared and aligned to the disclosed promoter sequences. Sequence homology/identity can be determined through sequence alignment using computer software programs such as ALIGN, DNAstar, and INHERIT as well as through sequence alignment programs such as BLAST and BLAST2 available from the National Center for Biotechnology Information (URL address http://www.ncbi.nlm.nih.gov/BLAST/).

Transformation of Plants:

A variety of different techniques well known by those skilled in the art, including biological and physical plant transformation protocols, can be used to insert the heterologous genes into a plant host. Suitable methods include microorganism-mediated gene transfer, such as transfection using an Agrobacterium-mediated transfection system (Horsh et al., 1985, *Science* 227:1229–1231; Hiei et al., 1994, *Plant J*. 6:271–282; Ishida et al., 1996, *Nat. Biotechnol*. 14:745–750; Tingay et al., 1997, *Plant J*. 11:1369–1376; McCormac et al., 1998, *Euphytica* 99:17–25), electroporation (see for example, D'Halluin et al., 1992, *Plant Cell* 4:1495–1505; Laursen et al., 1994 *Plant Mol. Biol*. 24:51–61), and microprojectile bombardment (Wan and Lemaux, 1994, *Plant Physiol.* 104:37–48; Jensen et al., 1996, supra). All of these techniques involve the use of DNA vectors for delivery of the nucleotide sequences to be transferred to the plant cell. Vectors suitable for use in the present invention include, but are not limited to vectors carrying the α-glucosidase gene promoter or cystatin-1 gene promoter from cereal grains, preferably barley. However, the actual method of introduction of DNA is not critical with respect to the invention.

In a broad sense, the invention thus provides a process for the production in a plant host of heterologous protein, by growing plants or plant cells that, by means of genetic manipulation have been provided with the genetic information which is required to allow the plant host to express the heterologous protein material during germination.

According to the invention, the heterologous proteins expressed during germination may be synthesized as non-secreted molecules on free ribosomes in the cytoplasm of the plant cells.

Another aspect of the invention concerns the expression of pre-proteins during germination of plant cells. Many secreted proteins are synthesized in a precursor form. This precursor molecule contains an amino-terminal extension of 15–30 amino acids, denoted a signal sequence or a signal peptide. There is great variability as to the length and the sequence of these peptides. In spite of this variation, there are some general structural characteristics which must be satisfied in order for these peptides to be correctly processed by signal peptidases (von Heijne, 1986 *Nucleic Acids Res.* 14:4683–4690). These peptidases preferentially recognize certain amino acid sequences. Some caution is needed however, since the cleavage specificity also depends on the amino acids following the carboxy-terminus of the signal peptide.

The present invention details the prediction of the site for signal peptidase cleavage of the barley α-glucosidase pre-enzyme and the barley cystatin-1 precursor polypeptide, and Example 4 furthermore shows that the barley α-glucosidase signal sequence can establish secretion and processing of heterologous proteins to the extracellular space of a plant cell.

The present invention can be used to make a variety of transgenic plants, and the invention is particularly suited for use with cereal grains that are used for industrial malting purposes.

The following examples are meant to illustrate, but in no way to limit, the claimed invention.

EXAMPLE 1

Cloning of the a-Glucosidase Promoter

A clone was obtained from a published barley cDNA library (Leah et al., 1991, *J. Biol. Chem.* 266:1564–1573). It was sequenced and found to consist of a 2392-bp DNA fragment, denoted Fragment A. This sequence was subsequently shown to comprise nucleotides 385–2725 of plasmid pAGL.2752, which contains a cDNA sequence for α-glucosidase of barley cultivar Morex (Tibbot and Skadsen, 1996, supra; GenBank Accession No. U22450). Fragment A was labelled with $^{32}$P-dCTP according to the protocol of the Multiprime Labelling System (Amersham), and subsequently used as a probe for screening a commercial barley genomic library in the Lambda FIXW II vector (Stratagene; Cat. No. 946104), following the instructions recommended by the manufacturer of the library.

The library of about 0.5×10$^6$ plaque forming units was screened for recombinant phage containing sequences homologous to the α-glucosidase cDNA clone by in situ plaque hybridization. Filters were Protan BA85 nitrocellulose membranes (Schleicher & Schuell), which were prehybridized for 1 hour at 42° C. in 5×SSC (1×SSC=0.15 M NaCl, 0.025 M Na-citrate), 5× Denhardt's medium, 50% formamide, 100 μg/mL denatured, sonicated salmon DNA, 10 μg/mL polyadenylic acid and 0.2% SDS. Hybridization was at 42° C. for 16 hours with $^{32}$P-labelled Fragment A as probe. Filters were subsequently washed 3×15 minutes at 22° C. in 2×SSC, 0.2% SDS, followed by three washes, each for 5 min at 65° C. in 0.2×SSC, 0.1% SDS. Autoradiography was carried out at −80° C. for 16 hours, using Kodak XAR5 Film. Alignment of the developed film with the nitrocellulose membranes made it possible to identify two plaque areas of nucleic acid material which hybridized to the $^{32}$P-labelled probe. Following two re-screenings as detailed in the instructions for screening of the genomic library (Stratagene), it was eventually possible to identify one plaque which was expected to consist of Lambda phage particles harbouring DNA which corresponded to the genomic sequence for the barley α-glucosidase gene.

Purified phage DNA from said plaque was digested with SacI-NotI, and some of the resulting fragments were subcloned in pBluescript SK-(Stratagene). Plasmid DNA was prepared and sequenced using an ABI 373 DNA sequencer (Perkin-Elmer), following the manufacturer's instructions. DNA sequence analysis demonstrated that a genomic DNA fragment corresponding to the cDNA for barley α-glucosidase had been isolated. A restriction site map of the genomic clone is presented in FIG. 1A, and FIG. 2 shows the DNA sequence of the gene promoter [SEQ ID NO: 1], signal peptide coding region [SEQ ID NO: 3] of the barley gene for α-glucosidase, and the deduced amino acid sequence of the barley α-glucosidase signal peptide [SEQ ID NO: 4].

Figure 1B:
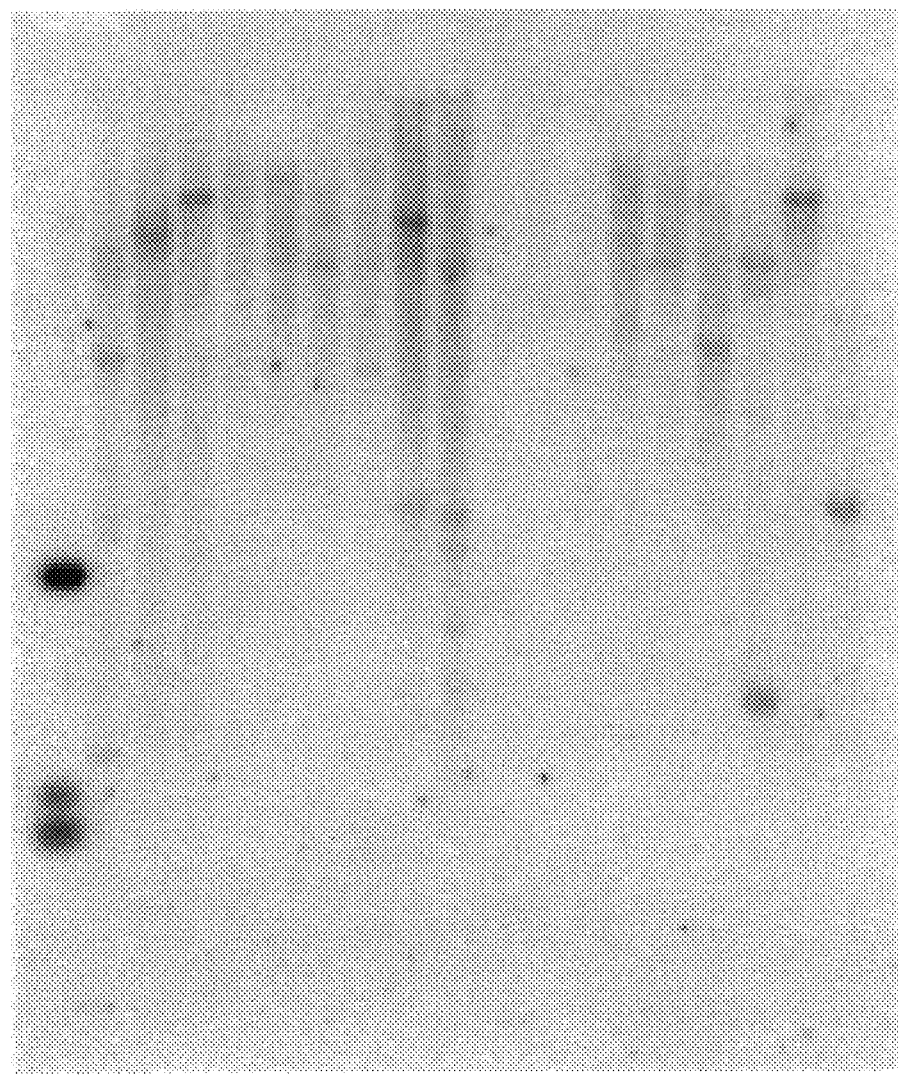

To identify α-glucosidase genes in the genomes of other cereals than barley, a genomic Southern blot analysis was performed (FIG. 1B). Genomic DNA was purified from leaves of barley, wheat, rice, maize, rye and sorghum according to the protocol of the Plant DNA Isolation Kit (Boehringer; Cat. No. 1667319). DNAs were digested with restriction enzymes, and 15 μg of each sample fractionated on a 1.0 % agarose/TBE gel (TBE=89 mM tris[-hydroxymethyl]aminoethane, 89 mM boric acid, 2 mM EDTA-NaOH; pH 8.0), and transferred to a Hybond™-N membrane (Amersham) by the capillary blotting method (Southern, 1977, supra). Subsequently, Fragment A was labelled as described above. The methods for pre-hybridization, hybridization, washing of the blot and autoradiography were as described above, except that hybridization conditions were 1.0×SSC, 0.1% SDS at 65° C., and autoradiography was carried out for 80 hours as detailed by the instruction for using a Storm® system (Molecular Dynamics).

Signals from one or few hybridizing DNA fragments were detected in all lanes of the genomic Southern blot (FIG. 1B). Accordingly, it is concluded that the cereals contain DNA fragments harbouring gene sequences which share homology with the Fragment A probe, where said probe comprises the barley α-glucosidase gene.

EXAMPLE 2

Prediction of Signal Peptidase Cleavage Site

Although the entire pre-protein sequence of barley α-glucosidase is known and the enzyme is known to be secreted, the position of signal peptidase cleavage has not been determined. In order to obtain a qualified prediction of the signal peptidase cleavage site of the barley α-glucosidase pre-protein, its amino-terminal 50 amino acid residues were analysed using the SignalP program (Center for Biological Sequence Analysis, Danish Technical University, Denmark; Nielsen et al., 1997, *Prot. Eng.* 10:1–6). The program utilizes a neural network for prediction of signal peptidase cleavage sites, and returns the result of an analysis as a C-score, an S-score and a Y-score. The C-score is the raw cleavage site score, with a high value immediately after the cleavage site; the S-score is high at all positions upstream of the cleavage site, and low after the cleavage site; the Y-score is a geometric average between the C-score and a smoothed derivative of the S-score.

Figure 3A:
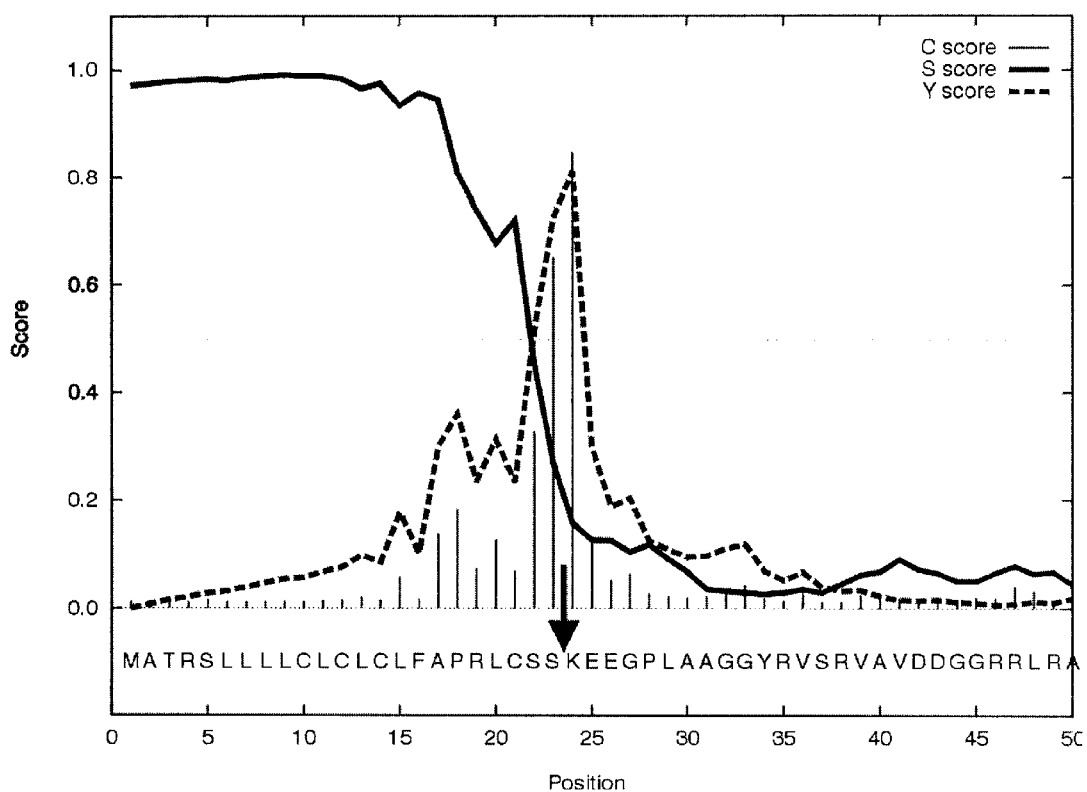
FIGS. 3A and 3B is a graphical representation used for prediction of signal peptidase cleavage sites for pre-proteins of barley α-glucosidase and barley high-pI α-amylase. A vertical arrow indicates the site of processing. More detailed information on C-, S-, and Y-scores is given in Example 2.
Figure 3B:
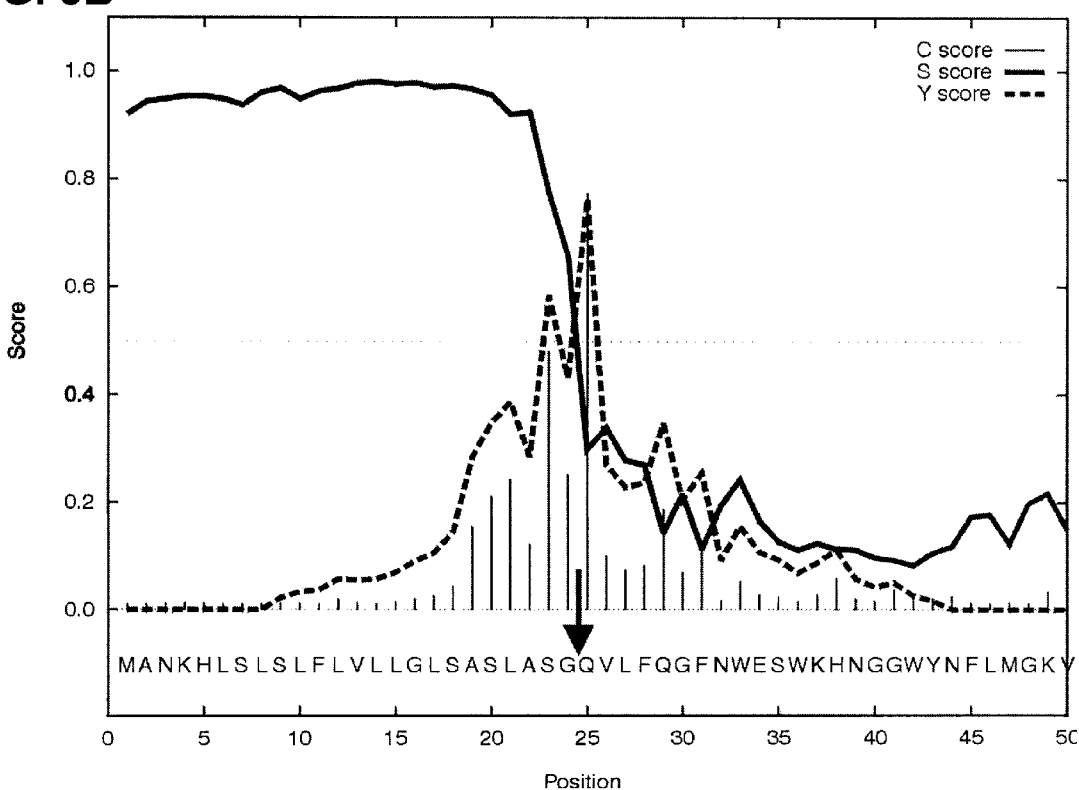

As illustrated in FIG. 3, signal peptidase cleavage of the barley α-glucosidase pre-protein is predicted to be between amino acid residues serine-23 and lysine-24. For comparison, and shown in FIG. 3, the SignalP program predicted the signal peptidase cleavage site of barley high-pI α-amylase to be between glycine-24 and glutamine-25, corresponding to the actual in vivo cleavage site of the homologous pre-protein (Kadziola et al., 1994, *J. Mol. Biol.* 239:104–121).

EXAMPLE 3

Constructs for Expression of Heterologous Genes

For the expression of the gene encoding heat stable (1-3,1-4)-β-glucanase H(A12-M)ΔY13, the following regulatory sequences were used:

a. The promoter of the gene for barley high-pI α-amylase (Khursheed and Rogers, 1988, supra; nucleotides 441–1176 of GenBank Accession No. K02637). This gene promoter is an integral part of plasmids pCT1 and pCT2, previously denoted pAMY-αH(A12-M)ΔY13-GC-N and pAMY-αH (A12-M)ΔY13-N, respectively, by Jensen et al. (1996, supra). pCT1 contains a G-C rich DNA sequence encoding heat stable (1-3,1-4)-β-glucanase H(A12-M)ΔY13. pCT2 is identical to pCT1, except that the sequence encoding (1-3, 1-4)-13-glucanase H(A12-M)ΔY13 is not G-C rich.

b. The promoter of the gene for barley α-glucosidase [SEQ ID NO: 2], i.e. nucleotides 947–1930 in FIG. 2.

c. The transcription termination sequence derived from the gene coding for nopaline synthase (nos) of the pTiC58 plasmid from *Agrobacterium tumefaciens* (Bevan, 1984, *Nucleic Acids Res.* 12:8711–8721; nucleotides 1565–1823 of GenBank Accession No. U12540).

d. The transcription terminator sequence of the pea gene encoding ribulose 1,5-bisphosphate carboxylase (Morelli et al., 1985, *Nature* 315:200–204; nucleotides 956–1277 of GenBank Accession No. X04334).

An overview map of the six constructs used is given in FIG. 4. The vector parts of the expression plasmids are not shown in FIG. 4. However, the vector parts do not differ on points that are relevant for the present invention.

Techniques for nucleic acid manipulation of genes of this invention such as subcloning nucleic acid sequences into vectors, PCR amplifications are generally described in Sambrook et al., 1989, *Molecular Cloning—A Laboratory Manual* (2nd Ed.), Vol. 1–3, Cold Spring Harbor Laboratory, Cold Spring Harbor, N.Y.

Construction of the plasmids containing the barley α-glucosidase gene promoter started from a plasmid harbouring the SacI-NotI fragment consisting of said gene promoter (FIG. 1B). First, the TCC codon for the carboxyl-terminal serine residue of the α-glucosidase signal sequence was mutagenized to AGC, also specifying serine, thus introducing an XhoI restriction site close to the site which corresponds to signal peptidase cleavage of the putative α-glucosidase pre-protein (the resulting-sequence spanning the α-glucosidase gene promoter and signal sequence code is denoted Fragment a). In parallel, the synthetic DNA sequence encoding mature H(A12-M)ΔY13, adapted for expression in barley aleurone tissue as described by Jensen et al. (1996, supra), was extended at its 5' end with a sequence for an XhoI restriction site (the resulting sequence spanning the sequence for mature H(A12-M)ΔY13-nos terminator is denoted fragment b). Fragment a and fragment b were ligated and cloned into vector pcDNA2.1 (Invitrogen), giving plasmid pCT4 (FIG. 3), specifying the sequence for barley α-glucosidase signal sequence in frame with the sequence for mature H(A12-M)ΔY13.

Construction of plasmid pCT3 (FIG. 3), which is identical to plasmid pCT4 (FIG. 3) except that the DNA sequence for the signal peptide sequence is that for the corresponding sequence of barley high-pI α-amylase (Jensen et al., 1996, supra), was constructed by first amplifying by PCR a DNA fragment denoted fragment C, which comprises the α-glucosidase gene promoter fused to the part of the sequence for the barley α-amylase high-pI signal sequence which includes the restriction site for SfiI. Fragment C was ligated with the H(A12-M)ΔY13-specifying SfiI-EcoRI fragment of plasmid pCT1 (FIG. 3), thus yielding plasmid pCT3 where the barley α-glucosidase gene promoter is expected to direct synthesis of H(A12-M)ΔY13 as a pre-protein, which eventually is secreted as a mature enzyme from barley cells.

Plasmid pCT5 (FIG. 3) contains the gene promoter of the barley gene for high-pI α-amylase upstream of the reporter sequence encoding β-glucuronidase. Downstream of the reporter gene is the terminator sequence for the gene encoding pea ribulose 1,5-bisphosphate carboxylase. pCT5 was constructed by first amplifying the gene promoter segment with primers that introduced a HindIII and a BamHI site at the 5' and 3' end, respectively, followed by ligation into a HindIII-BamHI linearized plasmid Chi26/GUS (Leah et al., 1994, *Plant J.* 6:579–589). The transcription termination sequence of the plasmid Chi26/GUS series is that of the rbcS-3C terminator sequence (Morelli et al., 1985, supra).

Plasmid pCT6 (FIG. 3) is identical to pCT5, except that pCT6 contains the barley gene promoter for α-glucosidase, where said promoter had been amplified with primers that introduced a HindIII site at the 5' end and a BamHI site at the 3' end.

EXAMPLE 4

Expression of Proteins Directed by α-Glucosidase Promoter

Assays for Analysis of Transient Gene Expression

It is possible to evaluate the expression levels directed by the barley α-glucosidase gene promoter by several methods. One such method is by transient expression assays performed with protoplasts prepared from aleurone layers of the barley cultivar Himalaya. This approach is not only used to evaluate the ability of different promoters to function in barley endosperm-derived tissues, including the aleurone tissue, but also to determine whether an expressed protein is secreted from the plant cell or whether the protein remains in the cell cytoplasm.

Protoplasts are transfected with a gene cassette of interest and incubated to allow the introduced gene to be expressed, and the corresponding protein allowed to accumulate in the cell or in the surrounding liquid medium. Following incubation at 25° C. for 40 hours in the presence or absence of gibberellic acid, the cells and the growth medium are assayed for the presence of the protein encoded by the transgene in order to determine the efficiency of the promoter which drives transgene expression.

A protocol for the preparation and transfection of barley aleurone protoplasts has been published by Skriver et al., (1991, supra). Forty hours after transfection, individual transfected protoplast cultures, each of 1 mL, is subjected to centrifugation and separated in a protoplast fraction (containing non-secreted protein), and a supernatant fraction (containing secreted proteins). Both fractions are immediately assayed for the enzymic activity derived from the heterologous gene product. While enzymes in the growth medium often can be assayed without special sample treatment, the protoplasts are broken by gentle grinding in 200 μL of enzyme assay buffer, cell debris pelleted by centrifugation, and the cleared supernatant assayed for enzymic activity of the heterologous gene product. Data from such experiments, utilizing plasmids shown in FIG. 4 and described in Example 3 of this specification, are presented in FIGS. 5 and 6.

The assay for measuring (1-3,1-4)-β-glucanase activity is based on the procedure recommended by the supplier of a kit for the assay of malt β-D-glucanase (Megazyme, product No. K-MBGL), except that incubations were carried out at 50° C. or 65° C., temperatures at which endogenous barley (1-3,1-4)-β-glucanases exhibit very low activity. Additionally, protoplasts transfected with pCT5 and pCT6 (FIG. 4) were assayed for β-glucuronidase activity using a fluorometer, following the protocol detailed by Leah et al. (1994, supra). In other experiments, barley aleurone proteins from protoplast and supernatant fractions were separated by SDS-polyacrylamide gel electrophoresis, then transferred by western blotting onto an Immobilon-P membrane (Millipore), and subsequently immunodetected with a rabbit antibody against H(A12-M)ΔY13 (Dako). Following binding with goat anti-rabbit peroxidase, H(A12-M)ΔY13 was visualized with specific staining for peroxidase activity, using the procedure detailed for the use of Fast BCIP/NBT substrate tablets (Sigma, product No. B-5655).

Figure 6:
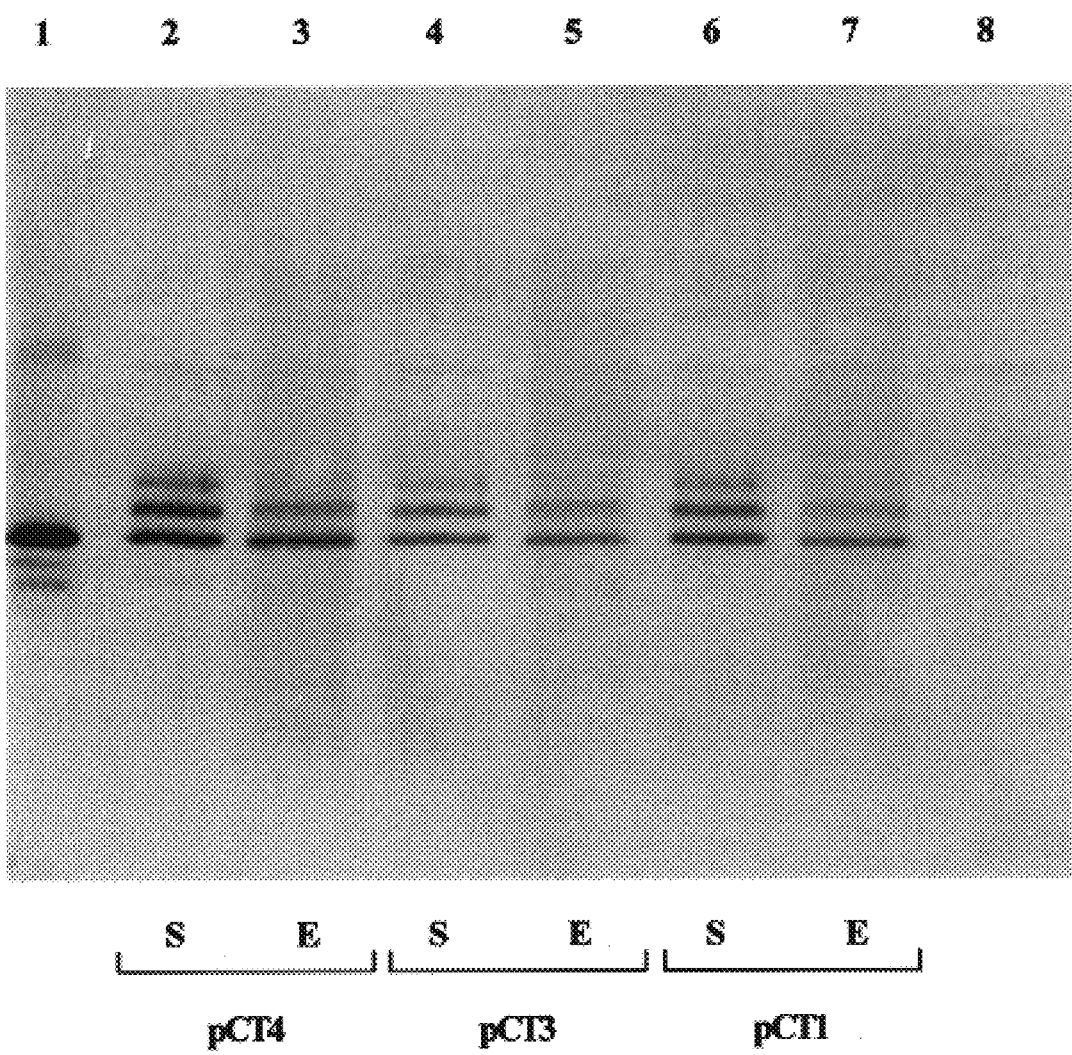
FIG. 6 is a Western blot of proteins from 8 μl of growth medium (S) and 8 μl of extract (E) fractions of protoplasts transfected with pCT4 (lane 2 and 3), pCT3 (lane 4 and 5), and pCT1 (lane 6 and 7). Lane 1 contained 20 ng of (1-3,1-4)-β-glucanase H(A12-M)ΔY13 which had been purified from a culture of transformed *Escherichia coli* cells (Politz et al., 1993, *Eur. J. Biochem* 216:829–834), and lane 8 contained proteins from 8 μl of supernatant from a protoplast preparation which was transfected with a control plasmid harbouring an irrelevant insert.

The results of such experiments is presented in FIG. 6. The presence of 2 to 3 stained protein bands reflects the presence of several glycoforms of H(A12-M)ΔY13 as pointed out by Jensen et al. (1996, supra). Taken together, the results from transfection experiments with barley aleurone protoplasts support that the barley α-glucosidase gene promoter directs heterologous expression comparable in efficiency to that of the promoter for barley high-pI α-amylase. The promoter of the gene for barley α-glucosidase responds to gibberellin, since enhanced levels of activity derived from heterologously expressed enzymes are seen following incubation of protoplasts in the presence of gibberellic acid.

Moreover, the signal sequence of barley α-glucosidase is able to direct heterologous proteins to the exterior of the cell. Differences in activity levels between constructs harbouring DNA sequences that specify the signal sequences of α-amylase and α-glucosidase may be the result of differences in efficiency or specificity of signal peptidase cleavage, similar to the situation when various signal sequences were used for secretion of a heterologous protein from yeast (Olsen and Thomsen, 1989, Carlsberg Res. Commun. 54:29–39). Accordingly, the efficiency of signal peptidase cleavage of pre-proteins harbouring the signal sequence of barley α-glucosidase is expected to depend not only on the signal sequence per se, but also on the protein part downstream of the signal sequence.

Figure 5A:
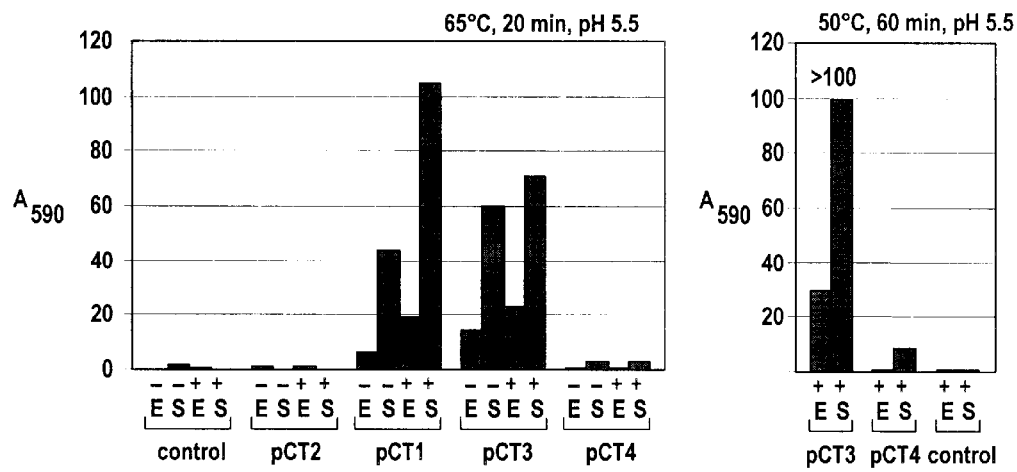
FIGS. 5A–5C are a series of bar graphs presenting enzymic activities from assays of aleurone protoplasts of barley cultivar Himalaya after transfection with plasmids pCT1 to pCT6 (details of plasmids are shown in FIG. 4), and a plasmid, denoted "control", harbouring control, non-glucuronidase insert. The results shown were obtained using aliquots of three individually prepared protoplasts suspensions; one suspension for the results shown in FIG. 5A, one suspension for the results shown in FIG. 5B, and one suspension for the results shown in FIG. 5C. Protoplast aliquots were incubated in the presence (indicated with "+") or absence (indicated with "−") of gibberellic acid. Total enzymic activities in protoplast extract (E) and growth medium (S) fractions of protoplast suspensions were determined following incubation conditions as listed above the relevant section of the figure. Activity derived from (1-3,1-4)-β-glucanase H(A12-M)ΔY13 was measured as absorbance at 590 nm ($A_{590}$); the bar in FIG. 5A marked with ">100" indicates that the measured value was significantly higher than 100 $A_{590}$ units, possibly 400 to 500 $A_{590}$ units. β-Glucuronidase activity was measured as fluorescent units (FLU).
Figure 5B:
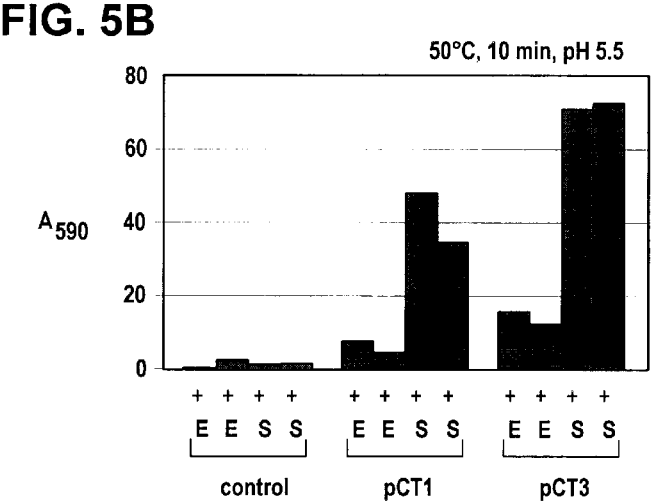
Figure 5C:
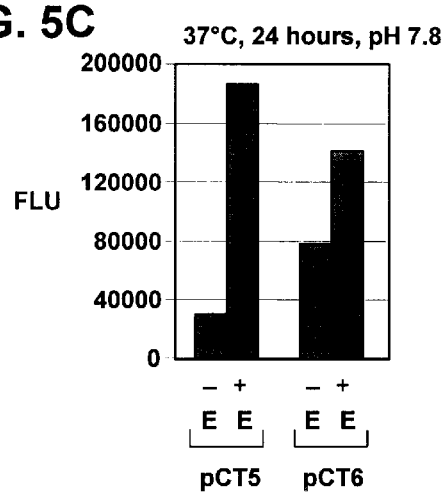

The successful implementation of the invention in the use of barley germination-specific promoters, such as the barley α-glucosidase gene promoter, to drive heterologous gene expression also depends on the coding sequence of the heterologous gene, such that the codon usage of said gene is compatible with the tRNA population in the germinating grain tissue (Jensen et al., 1996 supra). The importance of codon usage is illustrated in FIG. 5A, where a heterologous gene with non-modified codons (pCT2) and a low GC content gives very low levels of expression, as measured by gene product activity, in comparison to a heterologous gene synthesized with barley aleurone gene codon usage (pCT1).

Enzymatic Activity of Expressed Fusion Constructs

Another method to evaluate the expression levels directed by the barley α-glucosidase promoter involves constructing an expression cassette, for example as a fusion between the barley α-glucosidase gene promoter and a gene for heat stable (1-3,1-4)-β-glucanase H(A12-M)αY13, as shown in FIG. 4, and determining the enzymic activity derived from heat stable (1-3,1-4)-β-glucanase within germinating, transgenic barley grains.

Transformed plant lines, identified by PCR screening for the presence of transgene, are grown to maturity. Transformed lines expressing enhanced levels of heat stable (1-3,1-4)- β-glucanase H(A12-M)ΔY13 during germination are identified as described by Jensen et al. (1996, supra). After selection of transgenic plants, histochemical analyses are performed on plant tissues at various stages of development to determine both tissue- and cell type-specificity. This technique is commonly used to evaluate promoter activity in both monocots and dicots.

Homozygous, transgenic plants are generated, and kernels from subsequent generations of off-spring plants harvested for further propagation (see Jensen et l., 1998, supra). In this way, sufficient material is generated for industrial use.

EXAMPLE 5

Cloning the Gene Encoding Cystatin-1

A cDNA library was constructed from total RNA isolated from de-embryonated barley kernels of cultivar Alexis sampled 32 hours after the start of an industrial malting procedure. The RNA was extracted with a FastRNA Kit-Green (BIO101), and used as template for synthesis of cDNA using the SMART™ PCR cDNA Synthesis Kit (Clontech). cDNA fragments were then ligated and cloned into vector pcDNA2.1 (Invitrogen). DNA sequencing of the resulting cDNA clones identified one clone with a 503-bp insert comprising an open reading frame of 429 nucleotides [SEQ ID NO: 5], shown in FIG. 7, encoding a protein of 142 amino acid residues [SEQ ID NO: 6], also shown in FIG. 7. This amino acid sequence was found to be 66% identical to oryzacystatin I (GenBank Accession No. M29259), 58% identical to a rice oryzacystatin II (GenBank Accession No. X57658), and 70% identical to maize cystatin II (GenBank Accession No. X87126). Accordingly, the cloned barley cDNA sequence is derived from the cys1 gene encoding a barley cystatin polypeptide, in this invention denoted cystatin-1.

Identification of a sequence for cystatin-1 in a de-embryonated germinating barley kernel cDNA library indicates that the corresponding cys1 gene is transcribed in endosperm cells, more specifically in the living aleurone cells of the endosperm.

Genomic DNA, isolated from etiolated leaves of barley cultivar Alexis seedlings using the methods provided by the supplier of the FastDNA™ Kit (BIO101), served as template for PCR amplifications of the genomic sequence encoding cystatin-1. The gene promoter and part of the protein coding region was amplified by thermal asymmetric interlaced (TAIL-) PCR using reaction conditions for primary, secondary and tertiary amplifications as detailed by Liu et al. (1995, *Plant J.* 8:457–463). Primer 5'-(A/T)GTG-NAG(A/T)A-NCANAGA-3', identical to AD3 (Liu et al., 1996, supra), was used with primer 5'-TCTCGAACTCCAGCAGGGCAT-3' [SEQ ID NO: 9] (primer A in FIG. 7), primer 5'-CATTGGCCTTCTTGTTGTGCT-3' [SEQ ID NO: 10] (Primer B in FIG. 7), and primer 5'-GTCGTTCTCTTGTCCCATC-3' [SEQ ID NO: 11] (Primer C in FIG. 7) in the primary, secondary and tertiary amplification, respectively. The single PCR product which was amplified in the tertiary reaction was cloned into vector pcDNA2.1 (Invitrogen), giving plasmid pCys1prom.

Primer 5'-ATGGAGATGTGGAAATATCGG-3' [SEQ ID NO:12] and primer 5'-TTATGCAATTGCAGCGTCCTGC-3' [SEQ ID NO: 13], in FIG. 7 and FIG. 8 denoted Primer D and Primer E, respectively, were used to amplify the sequence spanning the start and stop codons of the barley gene for cystatin-1. The resulting DNA fragment was subsequently cloned into vector pcDNA2.1 (Invitrogen), yielding plasmid pCys1 ORF.

Inserts of plasmids pCys1prom and pCys1ORF were sequenced on an ABI 373 DNA sequencer (Perkin-Elmer) using the manufacturer's instructions. Comparison of the insert sequences generated a 2333-nucleotide long DNA sequence [SEQ ID NO: 15], comprising the gene promoter and protein coding region (schematically shown in FIGS. 8-1 through 8–3). The 1508-bp gene promoter sequence located 5' to the open reading frame for cystatin-1 comprises a putative CAAT box (spanning nucleotides 1413 to 1416 of FIG. 8) and a putative TATA box (spanning nucleotides 1484 to 1490 of FIG. 8).

A single intron sequence of 396 bp interrupts the protein coding region at nucleotide no. 1742 of the genomic sequence. Except for this intron, there are no differences in protein coding sequence between the cDNA and genomic sequence.

It should be noted that the 3' nucleotide (i.e. "A") of primer AD3 (Liu et al., 1995, supra) is not present in the gene promoter sequence. The molecular basis for this base deletion remains elusive.

EXAMPLE 6

Expression of the Barley Gene Cys1

Northern analysis revealed that the cys1 gene was selectively expressed in germinating barley. Developing barley kernels were harvested 14, 20 and 30 days after fertilization, and germinating kernels were sampled during laboratory germination (incubation at 15° C. in Petri dishes in the dark) and during industrial malting. Total RNA was isolated from the barley kernel samples according to a published procedure (Leah and Mundy, 1989, *Plant Mol. Biol.* 12:673–682), and 10 μg RNA was subsequently separated per lane on agarose gels. The gels were blotted onto Hybond™-N+ membranes (Amersham), which were hybridized sequentially with the 503-bp cDNA sequence derived from the cys1 gene (cf. Example 5), and the 900-bp cDNA clone E derived from the Amy6-4 gene (Rogers and Milliman, 1983, supra), both probes labelled with $^{32}$P-dCTP using the Megaprime DNA labelling kit (Amersham). Following hybridization, the filters were analysed using a Phosphoimager (Molecular Dynamics).

In barley kernels, the cys1 gene is specifically expressed during germination and not during kernel development. The barley gene Amy6-4 encoding high-pI α-amylase is highly expressed in the kernel during laboratory germination and at a reduced level during industrial malting (FIG. 9). This is consistent with repressed levels of hydrolytic enzyme synthesis seen under certain industrial malting conditions (Kitamura and Yumoto, 1990, *Monatschrift für Brauwissenschaft* 9: 310–315). The cys1 gene, however, is more highly expressed under industrial malting conditions than under laboratory conditions (FIG. 9). Since the barley gene promoter of cys1 directs expression of said gene in a temporal and tissue-specific manner, namely in the aleurone tissue of germinating kernel, it may be used to regulate the expression of heterologous genes in barley. Furthermore, since transcription of cys1 in germinating barley kernels is enhanced under industrial malting conditions the cys1 gene promoter may be used to direct enhanced expression of heterologous genes during industrial malting.

EXAMPLE 7

Prediction of Signal Peptidase Cleavage Site of Barley Cystatin-1

An open reading frame of the cDNA derived from cys1 encodes a polypeptide of 142 amino acid residues [SEQ ID NO: 6], which shares close sequence homology with other cereal cystatins, including maize and rice cystatin (cf. Example 5). The maize cystatin-1 cDNA λZC7 encodes a precursor polypeptide, which is larger than the mature 13-kDa cystatin found in maize kernels; the deduced signal peptide sequence consists of 30 amino acid residues (Abe et al., 1994, *J. Biochem.* 116: 488–492). Amino acid sequence alignment of the cystatin polypeptides encoded by the barley cys1 gene and maize λZC7 cDNA indicates that barley cystatin-1 is synthesized as a pre-protein comprising a signal peptide.

Figure 10A:
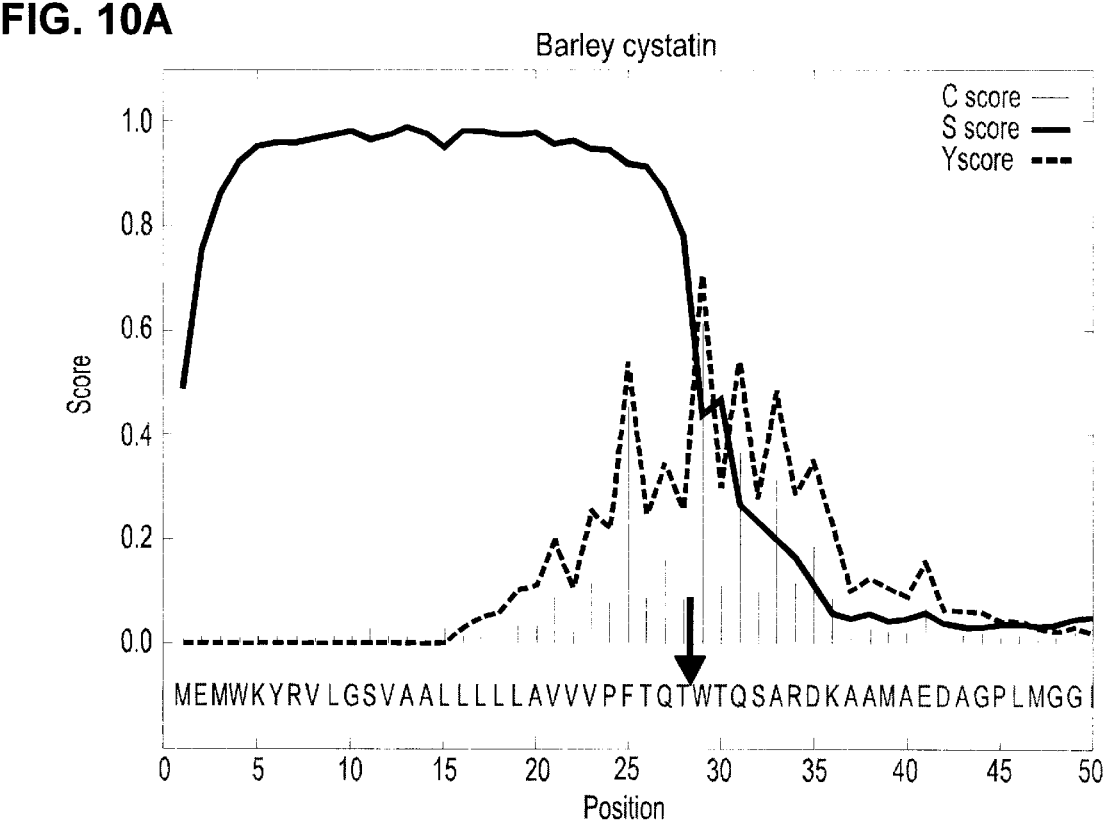
FIG. 10 is a graphical representation used for prediction of the signal peptidase cleavage site in the barley cystatin-1-pre-protein. A vertical arrow indicates the site of processing.
Figure 10B:
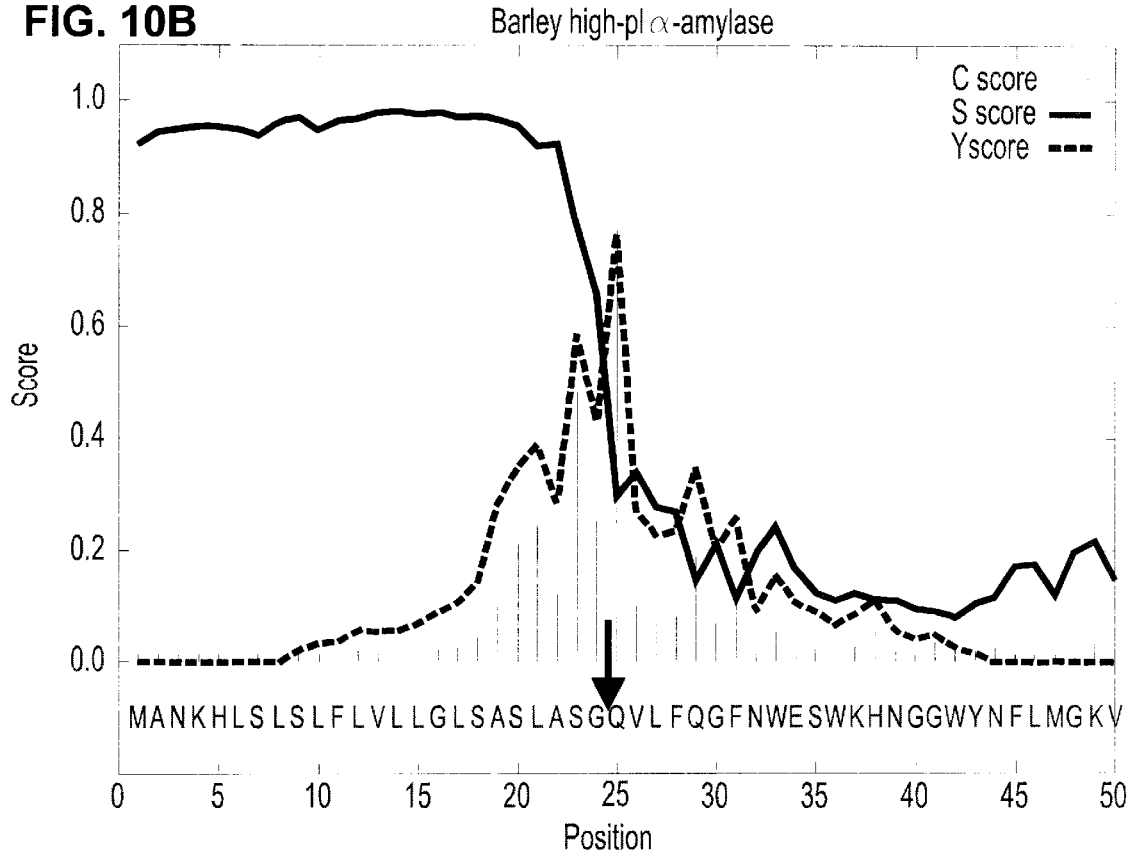

A qualified prediction of the signal peptidase cleavage site in the N-terminal 50 amino acids of the barley cystatin-1 pre-protein was obtained using the SignalP program (Center for Biological Sequence Analysis, Danish Technical University, Denmark; Nielsen et al., 1997, supra), as described in Example 2. As illustrated in FIG. 10, signal peptidase cleavage is predicted to occur between amino acid residues threonine-28 and tryptophan-29.

An amino-terminal peptide sequence comprising a signal peptide sequence and optionally the subsequent 1 to 10 amino acid residues to the carboxyl-terminal side of the signal peptidase cleavage site, may be expressed as a fusion protein with a heterologous protein, such that the signal peptide directs the heterologous protein into the secretory pathway. The nucleotide sequence of the barley cys1 gene, including the gene promoter, the sequence encoding the signal peptide and optionally the first 1 to 10 amino acid residues of the mature protein sequence, may be incorporated into gene constructs encoding heterologous proteins. The cyst gene promoter or a barley kernel tissue-specific gene promoter, operably linked to an open reading frame encoding the barley cystatin-1 signal peptide fused to a heterologous protein, may direct expression in the barley kernel and secretion of the chimeric gene product into the extracellular space. Several malt hydrolases, which play an essential role in the cereal malting process, are synthesized in barley aleurone cells and/or scutellum epithelium cells and are secreted into the endosperm tissue, where they contribute to the degradation of energy reserves during germination. The identification of a DNA sequence encoding an amino-terminal peptide sequence which comprises a signal peptide is therefore of particular value in the construction and use of heterologous genes encoding hydrolytic enzymes of importance for cereal malt quality.

EXAMPLE 8 cys1 Gene Promoter Constructs Useful to Direct Heterologous Protein Expression

Expression Plasmids

To evaluate the expression levels directed by the barley cystatin-1 gene promoter and identify regulatory elements required for promoter function, a series of expression plasmids comprising truncated promoter regions fused to the reporter gene encoding β-glucuronidase were constructed. Eight separate, standard PCR amplifications comprising plasmid pCys1prom (cf. Example 5) as template were performed, with antisense primer:

5'-TATATCTAGACTATCGGGGTCGGGATTTATA-3
[SEQ ID NO: 16] and sense primers:
5'-ATATAAGCTTCGAAGAGGTAAAACCCTACG-3'
[SEQ ID NO: 17],
5'-ATATAAGCTTAGGTTGCCATCAAGGAATAGA-3'
[SEQ ID NO: 18],
5'-ATATAAGCTTCCCTTACCACTCGCTGATG-3'
[SEQ ID NO: 19],
5'-ATATAAGCTTGCACAGTTCCTCGCTTGTC-3'
[SEQ ID NO: 20],
5'-ATATAAGCTTAATAAATCCAGCCGCACAC-3'
[SEQ ID NO: 21],
5'-ATATAAGCTTAAAATTTCGCCCTCGTCAC-3'
[SEQ ID NO: 22],
5'-ATATAAGCTTGCGTTTTGCTTCCATTTGTT-3'
[SEQ ID NO: 23], and
5'-ATATAAGCTTGCGACAGCATAGCGTGTAAC-3'
[SEQ ID NO: 24].

These reactions produced PCR fragments spanning the cystatin-1 gene promoter nucleotides 46 to 1504, 226 to 1504, 408 to 1504, 569 to 1504, 689 to 1504, 999 to 1504, 1084 to 1504 and 1274 to 1504, respectively (nucleotide numbering corresponds to that of FIG. 8).

Recognition sequences for HindIII (AAGCTT) and XbaI (TCTAGA) are located directly upstream of the sequences corresponding to the cystatin-1 gene promoter of the above mentioned sense and antisense primers, respectively. Following digestion with HindIII-XbaI, the PCR fragments were cloned into a HindIII-XbaI linearized pUC-derived reporter plasmid containing the gene encoding β-glucuronidase upstream of a 300-bp fragment carrying the polyadenylation sequence of the pea rbcS-3C gene as reported by Fang et al. (1989, Plant Cell 1:141–150), giving reporter plasmids pCysΔ45GUSrbc, pCysΔ225GUSrbc, pCysΔ407GUSrbc, pCysΔ568GUSrbc, pCysΔ688GUSrbc, pCysΔ998GUSrbc, pCysΔ1083GUSrbc and pCysΔ1273GUSrbc, where the plasmid notation directly following the symbol "Δ" denotes the number of bases deleted at the 5' end of the gene promoter sequence, as compared with pCys1ORF (cf. FIG. 8). Each of these plasmids contain the amplified gene promoter fragment of cys1 inserted at position −37 with respect to the translational start codon of the β-glucuronidase gene. The nucleotide sequence of each reporter plasmid insert was verified by DNA sequencing using an ABI 377 DNA sequencer as specified by the equipment supplier Perkin-Elmer.

Transient Expression in Plant Cells

Barley aleurone protoplasts were prepared as described in Example 4, and separate protoplast aliquots were co-transfected with plasmid pAHC18 carrying the luciferase gene under control of the gene promoter derived from a constitutively expressed maize ubitiquitin gene (Bruce et al., 1989, Proc. Natl. Acad. Sci. USA 86:9692–9696), and one of the eight expression plasmids containing 5' deletions of the cystatin-1 gene promoter, as described above. The molar concentration of pAHC 18 was half of that of the reporter plasmid directing expression of β-glucuronidase. Incubation of the protoplasts with 1 µM gibberellic acid or 1 µM abscisic acid were performed in order to analyse possible, regulative effects of the phytohormones on cys1 gene expression, and identify the location of possible hormone responsive cis-acting gene elements.

After a 40-hour incubation at 20° C., the protoplasts were harvested and the level of β-glucuronidase and luciferase activities determined as described by Leah et al. (1994, supra). The relative β-glucuronidase activity in individual samples was calculated by dividing the measured activity by the measured luciferace activity, thereby allowing differences in transformation efficiency to be corrected for.

Figure 11:
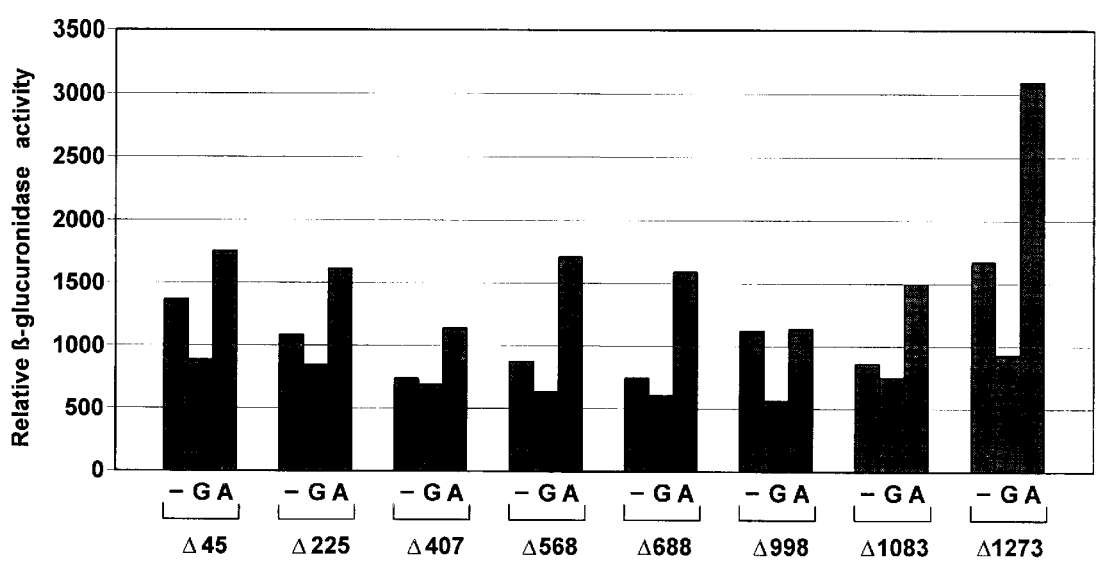
FIG. 11 is a series of bar graphs presenting enzymic activities from assays of aleurone protoplasts of barley cultivar Himalaya after transfection with plasmids pCysΔ45GUSrbc (Δ45), pCysΔ225GUSrbc (Δ225), pCysΔ407GUSrbc (Δ407), pCysΔ568GUSrbc (Δ568), pCysΔ688GUSrbc (Δ688), pCysΔ998GUSrbc (Δ998), pCysΔ1083GUSrbc (Δ1083), and pCysΔ1273GUSrbc (Δ1273). Details of plasmids are given in Example 8.

FIG. 11 summarizes the relative β-glucuronidase activities as calculated from data obtained following transfection of barley aleurone protoplasts with the eight cys1 promoter plasmid constructs, as detailed above. The results verify that the barley cystatin-1 gene promoter directs expression of the heterologous enzyme β-glucuronidase. Moreover, incubation of the aleurone protoplasts in the presence of gibberellic acid led to a slight depression in relative expression of β-glucuronidase, indicating that the gene promoter of cys1 is not positively regulated by the phytohormone. However, expression was increased following incubation in the presence of abscisic acid. Highest β-glucuronidase reporter enzyme activity was directed by plasmid pCysΔ1273GUSrbc which comprises the shortest gene promoter fragment, showing that the cis-acting abscisic acid response domain is likely to be located between nucleotides 1274 and 1504 of the gene promoter sequence (cf. FIG. 8).

Enzymatic Activity in Transgenic Plant Tissue

Another method to evaluate the expression levels directed by the barley cystatin-1 gene promoter involves constructing an expression cassette, for example as an operational linkage between the barley cystatin-1 gene promoter and a DNA sequence encoding heat stable (1-3,1-4)-β-glucanase H(A12-M)ΔY13, similar to that shown in FIG. 4, and determining the enzymic activity derived from heat stable (1-3,1-4)-β-glucanase within germinating, transgenic barley kernels.

Transformed plant lines, identified by PCR screening for the presence of the heterologous gene, are grown to maturity. Transformed lines expressing enhanced levels of heat stable (1-3,1-4)-β-glucanase H(A12-M)ΔY13 during germination are identified as described by Jensen et al. (1996, supra). After selection of transgenic plants, histochemical analyses are performed on plant tissues at various stages of development to determine both tissue- and cell type-specificity with respect to expression of the heterologous protein.

Homozygous, transgenic plants are generated, and kernels from subsequent generations of off-spring plants harvested for further propagation (see Jensen et al., 1998, supra). In this way, sufficient material is generated for industrial use.

This application contains reference to numerous publications and patents, each of which is hereby incorporated by reference for all purposes, as if fully set forth.

REFERENCES

Abe et al., J. Biochem. (1994) 116: 488–492
Abe et al., Biosci. Biotech. Biochem. (1996) 60:1173–1175

Bevan, *Nucleic Acids Res.* (1984) 12:8711–8721
Breathnach and Chambon, *Ann. Rev. Biochem.* (1981) 50:349–383
Brown and Dziegielewska, *Prot. Sci.* (1997) 6:5–12
Bruce et al., *Proc. Natl. Acad. Sci. USA* (1989) 86:9692–9696
D'Halluin et al., *Plant Cell* (1992) 4:1495–1505
Gelvin and Schilperoort, *Plant Molecular Biology Manual*, 2nd Edition, Kluwer Academic Publishers, Dordrecht, The Netherlands, 1998
Fang et al., *Plant Cell* (1989) 1:141–150
Gubler and Jacobsen, *Plant Cell* (1992) 4:1435–1441
Hiei et al., *Plant J.* (1994) 6:271–282
Horsh et al., *Science* (1985) 227:1229–1231
Ishida et al., *Nat. Biotechnol.* (1996) 14:745–750
Jensen et al., *Proc. Natl. Acad. Sci. USA* (1996) 93:3487–3491
Jensen et al., *Hereditas* (1998) 129:215–225
Kadziola et al., *J. Mol. Biol.* (1994) 239:104–121
Khursheed and Rogers, *J. Biol. Chem.* (1988) 263:18953–18960
Kitamura and Yumoto, *Monatschrift für Brauwissenschaft* (1990) 9:310–315
Kondo et al., *Gene* (1989) 81:259–265
Laursen et al., *Plant Mol. Biol.* (1994) 24:51–61
Leah and Mundy, *Plant Mol. Biol.* (1989) 12:673–682
Leah et al., *J. Biol. Chem.* (1991) 266:1564–1573
Leah et al., *Plant J.* (1994) 6:579–589
Liu et al., *Plant J.* (1995) 8:457–463
MacGregor et al., *J. Inst. Brew.* (1987) 93:334–337
McCormac et al., *Euphytica* (1998) 99:17–25
Mikkonen et al., *Plant Mol. Biol.* (1996) 31:239–254
Monroe et al., *Plant Physiol.* (1997) 115:863
Morelli et al., *Nature* (1985) 315:200–204
Nielsen et al., *Prot. Eng.* (1997) 10:1–6
Olsen and Thomsen, *Carlsberg Res. Commun.* (1989) 54:29–39
Politz et al., *Eur. J. Biochem.* (1993) 216:829–834
Rogers and Milliman, *J. Biol. Chem.* (1983) 258: 8169–8174
Sambrook et al., *Molecular Cloning—A Laboratory Manual* (2nd Ed.), Vol. 1–3, Cold Spring Harbor Laboratory, Cold Spring Harbor, N.Y., 1989
Skriver et al., *Proc. Natl. Acad. Sci. USA* (1991) 88:7266–7270
Southern, *J. Mol. Biol* (1977) 98:503–517
Sugimoto et al., *Plant Mol. Biol.* (1997) 33:765–768
Taylor et al., *Plant J.* (1998) 13:419–425
Tibbot and Skadsen, *Plant Mol. Biol.* (1996) 30:229–241
Tingay et al., *Plant J.* (1997) 11:1369–1376
Waldron et al., *Plant Mol. Biol.* (1993) 23:801–81
Wan and Lemaux, *Plant Physiol.* (1994) 104:37–48
Wolf, *Mol. Gen. Genet.* (1992) 234:33–42
Von Heijne, *Nucleic Acids Res.* (1986) 14:4683–4690
U.S. Pat. No. 5,712,112
U.S. Pat. No. 5,763,252

We claim:

1. An isolated α-glucosidase gene promoter comprising a polynucleotide selected from the group consisting of:
   (a) the nucleic acid sequence of SEQ ID NO:1;
   (b) the nucleic acid sequence of SEQ ID NO:2; and
   (c) a fragment of (a) or (b) that directs germination-specific gene expression of an operably linked heterologous nucleic acid sequence.

2. The promoter of claim 1, comprising the nucleic acid sequence of SEQ ID NO: 1 or SEQ ID NO: 2.

3. An expression construct comprising the α-glucosidase gene promoter of claim 1 operably linked to a nucleic acid sequence encoding a heterologous protein, the gene promoter capable of directing germination-specific expression of said heterologous protein from said nucleic acid sequence in a plant.

4. The expression construct of claim 3, further comprising a nucleic acid sequence encoding a barley α-glucosidase signal sequence operably linked to the nucleic acid sequence encoding a heterologous protein.

5. The expression construct of claim 4, wherein the nucleic acid sequence encoding the signal sequence comprises the sequence of SEQ ID NO: 3.

6. The expression construct of claim 4, wherein the α-glucosidase gene promoter comprises the nucleic acid sequence of SEQ ID NO: 1 or SEQ ID NO: 2.

7. A vector, plasmid, or host cell comprising the expression construct of claim 3.

8. The vector of claim 7, wherein the α-glucosidase gene promoter comprises the nucleic acid sequence of SEQ ID NO: 1 or SEQ ID NO: 2.

9. A plant cell transformed with the expression construct of claim 3.

10. The plant cell of claim 9, wherein the α-glucosidase gene promoter comprises the nucleic acid sequence of SEQ ID NO: 1 or SEQ ID NO: 2.

11. A transgenic plant comprising the expression construct of claim 3.

12. The transgenic plant of claim 11, wherein the plant is a cereal plant.

13. The transgenic plant of claim 12, wherein the plant is a barley plant.

14. The transgenic plant of claim 11, wherein the α-glucosidase gene promoter comprises the nucleic acid sequence of SEQ ID NO: 1 or SEQ ID NO: 2.

15. A method for producing a heterologous protein in a cereal plant, comprising: transforming a cereal plant cell with a nucleic acid sequence encoding a heterologous protein operably linked to the α-glucosidase gene promoter of claim 1 and expressing said heterologous protein in said cereal plant.

16. The expression construct of claim 3, wherein the α-glucosidase gene promoter comprises the nucleic acid sequence of SEQ ID NO:1 or SEQ ID NO:2.

17. The method of claim 15, wherein the α-glucosidase gene promoter is selected from the group consisting of:
   a) SEQ ID NO:1; and
   b) SEQ ID NO:2.

18. Kernels suitable for malting or brewing comprising the α-glucosidase gene promoter of claim 1 operably linked to a nucleic acid sequence encoding a heterologous protein.

19. The kernels of claim 18, wherein the α-glucosidase gene promoter comprises the nucleic acid sequence of SEQ ID NO:1 or SEQ ID NO:2.

* * * * *

SEQUENCE LISTING

<160> NUMBER OF SEQ ID NOS: 24

<210> SEQ ID NO 1
<211> LENGTH: 1930
<212> TYPE: DNA
<213> ORGANISM: Hordeum vulgare

<400> SEQUENCE: 1

```
gagctcatgg ttttaaactg agatgaattt taattttggg tggtgtgatt ttcctgtcaa      60
tgtcacaaca cagattttcg tatcttccat gctaaacaca ttattggcca ttcccaaaca     120
taaatataaa gtttactccc atccatcatt catacacaag ccatggctga ccatcctcgg     180
atgtccccca acatttcaac tgttccgcaa gtttttgttta attattttt attatgctgg     240 agtgagcatt cttttttacga gcctctcttg tgcaatgaaa aatggtgtac tgatgttccg     300
caaaaaatga aagtaatagc ttggaaagct tcagcgcgca ctatctacaa tgctaggtaa     360
ggtggagcat catattggtg ttcgtgctac atgtgtgatc tgtggtatgg aggatggatc     420
aagttttcat atgctcgtta cttgttatca tgcacacgag ctttgggagc gtatgcggga     480
ggtttggcct ctccctccgc tagagcgact acaacattca gagaaggatt ggcttctttt     540
attattggat ggttgttcgg caactactag aagcatgatt attttgttag tgtggagaat     600
ctggaattta aggaatgata tagtccatga taaggatgct actcccacat acgtttcgtt     660 tgaattttttc caaagttatc gacggtccct tgataacgat caaatactcg tctgaggaga     720
taccaaaggg aaagatgcct ttgatcagta ctaataacgc gttcattgtg ccggtttcga     780
aactagcctt atgttggaca ccaccaccac agggacagtc tgcattatca tttgatggtt     840
ccttctcgac tgcaaatagt accgcggcga catgtatgat cttaaggagg tatgatgtag     900
tgttattttt gcggcataca tattcttatt tcattgcaat gatgcactcg aggctgagat     960
```

```
ccacacgata atgcaagata tggctgttgc aattcaacat acggatctac gttcaatttg    1020
actcgtccat ggctctatct acacttgttg atgactacgt tgaccgttct gcatacgctc    1080
atttgacttt gaagattaaa gcacttgtgg ttgatatgga gtttgttcca tcaaaattac    1140
atcgtgttca aaatagagta gcagattgtt tgataaggta tagtcgttct aagtgtacta    1200
catatgtgtg gttacacaaa tggtctcatt tatcaaggaa attttacctc tagactgtaa    1260
ctctattact ttgaaataaa actccttatt ttgttgggaa aaaaatacgg ttgtagaggt    1320
tcggttagaa atgccagatc tatgaatgca ctaggactca tcgcaaggtt acgtgcacgt    1380
cgagtcagag aaaatgtgtg gcctttgaaa atccatgct gccgtatacg ctcgaaatac    1440
gcacctgcct agtatactac gtagtatatc ttacacggac gattgattga atgaacgaac    1500
gaattaagaa acgcacgcag cgaggagggc gggccggtca gcgggagtct gcgtacgtgc    1560
tcaccccgcc cgtagaccac tcgccgctcg ccaccgttgc ggcaagtaac agcccactgg    1620
gtcttatcgc cggcaccggt cccgatgcgt cgaccgcagc cgccgccgac ggctctggaa    1680
ggaaggaaga cccgtaccgc gccatgccgt tacccctggg cgcgcggtgc cgggcaacgg    1740
ccggattcca tgatctgctc gcgtctcccc catgccatgc cgtgataccg aaccaaccgg    1800
ccaaccaaag cggccacgat tggtccattt ggacggccgg cgatcctata agtacaggtg    1860
ccatcgctcg ccgatcgaca cagcgacaag cgcaagaccg tcacacacac acacacacca    1920
gccccatccg                                                           1930

<210> SEQ ID NO 2
<211> LENGTH: 984
<212> TYPE: DNA
<213> ORGANISM: Hordeum vulgare

<400> SEQUENCE: 2
ctcgaggctg agatccacac gataatgcaa gatatggctg ttgcaattca acatacggat      60
ctacgttcaa tttgactcgt ccatggctct atctacactt gttgatgact acgttgaccg     120
ttctgcatac gctcatttga ctttgaagat taaagcactt gtggttgata tggagtttgt     180
tccatcaaaa ttcatcgtg ttcaaaatag agtagcagat tgtttgataa ggtatagtcg     240
ttctaagtgt actacatatg tgtggttaca caaatggtct catttatcaa ggaaatttta     300
cctctagact gtaactctat tactttgaaa taaaactcct tattttgttg ggaaaaaaat     360
acggttgtag aggttcggtt agaaatgcca gatctatgaa tgcactagga ctcatcgcaa     420
ggttacgtgc acgtcgagtc agagaaaatg tgtggccttt gaaaatcca tgctgccgta     480 tacgctcgaa atacgcacct gcctagtata ctacgtagta tatcttacac ggacgattga     540
ttgaatgaac gaacgaatta agaaacgcac gcagcgagga gggcgggccg gtcagcggga     600
gtctgcgtac gtgctcaccc cgcccgtaga ccactcgccg ctcgccaccg ttgcggcaag     660
taacagccca ctgggtctta tcgccggcac cggtcccgat gcgtcgaccg cagccgccgc     720
cgacggctct ggaaggaagg aagacccgta ccgcgccatg ccgttacccc tgggcgcgcg     780
gtgccgggca acggccggat tccatgatct gctcgcgtct ccccatgcc atgccgtgat     840 accgaaccaa ccgccaacc aaagcggcca cgattggtcc atttggacgg ccggcgatcc     900
tataagtaca ggtgccatcg ctcgccgatc gacacagcga caagcgcaag accgtcacac     960
acacacacac accagcccca tccg                                           984

<210> SEQ ID NO 3
```

<211> LENGTH: 69
<212> TYPE: DNA
<213> ORGANISM: Hordeum vulgare

<400> SEQUENCE: 3

```
atggcgacgc ggtcgctgct gctgctctgc ttgtgtctct gcttattcgc gccccgcctg      60
tgctcgtcc                                                              69
```

<210> SEQ ID NO 4
<211> LENGTH: 23
<212> TYPE: PRT
<213> ORGANISM: Hordeum vulgare

<400> SEQUENCE: 4

Met Ala Thr Arg Ser Leu Leu Leu Cys Leu Cys Leu Cys Leu Phe
 1               5                  10                  15

Ala Phe Arg Leu Cys Ser Ser
            20

<210> SEQ ID NO 5
<211> LENGTH: 429
<212> TYPE: DNA
<213> ORGANISM: Hordeum vulgare

<400> SEQUENCE: 5

```
atggagatgt ggaaatatcg ggtcctggga tcggttgctg ccctgctctt gctgctcgcc      60
gtcgtcgtgc cgtttactca gacctggacg cagagcgcgc gggacaaggc tgccatggcg     120
gaagacgcgg ggccgttgat gggaggcatc gaggactcgc cgatgggaca gagaacgac      180 ctcgacgtca tcgcgctcgc ccgcttcgcc gtctccgagc acaacaagaa ggccaatgcc     240
ctgctggagt tcgagaatgt ggtgaagctg aagaaacaaa ctgttgctgg caccatgtac     300
tacattacaa ttcgggtcac tgaaggtggg accaagaagc tctatgaagc taaggtgtgg     360
gagaaactat gggagaactt taagcagctt gaggagttca gccggtgca ggacgctgca      420 attgcataa                                                             429
```

<210> SEQ ID NO 6
<211> LENGTH: 142
<212> TYPE: PRT
<213> ORGANISM: Hordeum vulgare

<400> SEQUENCE: 6

Met Glu Met Trp Lys Tyr Arg Val Leu Gly Ser Val Ala Ala Leu Leu
 1               5                  10                  15

Leu Leu Leu Ala Val Val Pro Phe Thr Gln Thr Trp Thr Gln Ser
            20                  25                  30

Ala Arg Asp Lys Ala Ala Met Ala Glu Asp Ala Gly Pro Leu Met Gly
        35                  40                  45

Gly Ile Glu Asp Ser Pro Met Gly Gln Glu Asn Asp Leu Asp Val Ile
    50                  55                  60

Ala Leu Ala Arg Phe Ala Val Ser Glu His Asn Lys Lys Ala Asn Ala
65                  70                  75                  80

Leu Leu Glu Phe Glu Asn Val Val Lys Leu Lys Lys Gln Thr Val Ala
                85                  90                  95

Gly Thr Met Tyr Tyr Ile Thr Ile Arg Val Thr Glu Gly Gly Thr Lys
            100                 105                 110

Lys Leu Tyr Glu Ala Lys Val Trp Glu Lys Leu Trp Glu Asn Phe Lys
        115                 120                 125

Gln Leu Glu Glu Phe Lys Pro Val Gln Asp Ala Ala Ile Ala
    130             135             140

<210> SEQ ID NO 7
<211> LENGTH: 84
<212> TYPE: DNA
<213> ORGANISM: Hordeum vulgare

<400> SEQUENCE: 7
atggagatgt ggaaatatcg ggtcctggga tcggttgctg ccctgctctt gctgctcgcc    60
gtcgtcgtgc cgtttactca gacc                                          84

<210> SEQ ID NO 8
<211> LENGTH: 28
<212> TYPE: PRT
<213> ORGANISM: Hordeum vulgare

<400> SEQUENCE: 8

Met Glu Met Trp Lys Tyr Arg Val Leu Gly Ser Val Ala Ala Leu Leu
 1               5                  10                  15

Leu Leu Leu Ala Val Val Val Pro Phe Thr Gln Thr
            20                  25

<210> SEQ ID NO 9
<211> LENGTH: 21
<212> TYPE: DNA
<213> ORGANISM: Hordeum vulgare

<400> SEQUENCE: 9
tctcgaactc cagcagggca t                                             21

<210> SEQ ID NO 10
<211> LENGTH: 21
<212> TYPE: DNA
<213> ORGANISM: Hordeum vulgare

<400> SEQUENCE: 10
cattggcctt cttgttgtgc t                                             21

<210> SEQ ID NO 11
<211> LENGTH: 19
<212> TYPE: DNA
<213> ORGANISM: Hordeum vulgare

<400> SEQUENCE: 11
gtcgttctct tgtcccatc                                                19

<210> SEQ ID NO 12
<211> LENGTH: 21
<212> TYPE: DNA
<213> ORGANISM: Hordeum vulgare

<400> SEQUENCE: 12
atggagatgt ggaaatatcg g                                             21

<210> SEQ ID NO 13
<211> LENGTH: 23
<212> TYPE: DNA
<213> ORGANISM: Hordeum vulgare

<400> SEQUENCE: 13
ttaatgcaat tgcagcgtcc tgc                                           23

<210> SEQ ID NO 14
<211> LENGTH: 1508
<212> TYPE: DNA
<213> ORGANISM: Hordeum vulgare

<400> SEQUENCE: 14

| | | | | | |
|---|---|---|---|---|---|
| agtggagaag | catagggaca | atatttaccc | aggttcgggc | cctctcgaag | aggtaaaacc | 60 |
| ctacgtcctc | cttgattata | ttgttgtgtg | tatgacgatt | atatagtcga | tctaccgcga | 120 |
| gatcatatga | actaagccct | agatgagtag | gataatggtt | ctcccctcta | caatctaaac | 180 |
| cctctgagtt | atatagacat | caggggtacc | tagggttata | ctgggaggtt | gccatcaagg | 240 |
| aatagacatg | tcgattctac | catcttgact | tgggaggaca | caccaaggct | tacagatttc | 300 |
| cttcgtgaac | gcgtagttat | gttatagctc | ggccttccac | aaagcggccc | acctgtccat | 360 |
| cccacaagtg | atagaccggc | agtctgatga | tcccttagtc | ccggactccc | ttaccactcg | 420 |
| ctgatggttg | ttgtcagcca | gatcttctcg | cctcatatgc | tccccatagg | tattgtcgcc | 480 |
| gccaatgctc | gcatatttga | gagagtgata | gtgaagaaat | atgaaaatga | acggtgaagg | 540 |
| gatttttggc | ccgcccttgg | gaaaaaacgc | acagttcctc | gcttgtcccc | acacgtgcaa | 600 |
| ccccgtggcc | tagatgttcc | tactcacgtc | tgacttcctg | gaaatgttcg | atcggtcgtt | 660 |
| cctccaaact | caaactctga | gctgctttaa | taaatccagc | cgcacacgtg | tacttcctcc | 720 |
| gtctcaaaat | aagtagctta | ttacaatttt | atactaaaac | tattacaaag | ttgagatagt | 780 |
| tattttaaaa | tggaggaagt | aggtaacaaa | gtgggacaaa | tttgatcccc | acggaattcc | 840 |
| tttatctttg | caaatccaag | caatctaatg | gattttctag | ggtcaagcat | gagtgtgaat | 900 |
| taaggatcaa | gcaaaacttc | tggacagata | agcatcaact | tgtcagttgt | cacagataca | 960 |
| cgcatgcgta | atgagtcata | tacatataca | tacgtggcaa | aatttcgccc | tcgtcacttc | 1020 |
| attacgactt | ataatcttga | cttaaaccca | agaattcgca | cccagttttt | tcatttcagc | 1080 |
| aaggcgtttt | gcttccattt | gttatcccag | ctttgctcct | ctgtcatcca | tggatccacc | 1140 |
| catataggaa | gatagaaaag | gataatcccc | ttattgttct | tgttgacttt | tgcatgaaca | 1200 |
| aggaaatcag | aagataaaca | tctagcctag | ggagaaggaa | ggaatccagc | cgagacccac | 1260 |
| agtgtcgcca | ttggcgacag | catagcgtgt | aacctaagct | gtaaaccct | cgggattggg | 1320 |
| gaaaagggcc | gtggtaggac | ccaacgatgc | ggggcccgtc | cattctattc | cgtccgttcc | 1380 |
| cgtgtcccgt | ccagactcag | agtgtcccca | cacaataatt | tcgccgacgg | atcgtactcc | 1440 |
| taccttctc | cccccaatac | cgggcctgct | ctgctactgc | agctataaat | cccgaccccg | 1500 |
| ataggtcg | | | | | 1508 |

<210> SEQ ID NO 15
<211> LENGTH: 2333
<212> TYPE: DNA
<213> ORGANISM: Hordeum vulgare

<400> SEQUENCE: 15

| | | | | | |
|---|---|---|---|---|---|
| agtggagaag | catagggaca | atatttaccc | aggttcgggc | cctctcgaag | aggtaaaacc | 60 |
| ctacgtcctc | cttgattata | ttgttgtgtg | tatgacgatt | atatagtcga | tctaccgcga | 120 |
| gatcatatga | actaagccct | agatgagtag | gataatggtt | ctcccctcta | caatctaaac | 180 |
| cctctgagtt | atatagacat | caggggtacc | tagggttata | ctgggaggtt | gccatcaagg | 240 |
| aatagacatg | tcgattctac | catcttgact | tgggaggaca | caccaaggct | tacagatttc | 300 |

-continued

```
cttcgtgaac gcgtagttat gttatagctc ggccttccac aaagcggccc acctgtccat    360
cccacaagtg atagaccggc agtctgatga tcccttagtc ccggactccc ttaccactcg    420
ctgatggttg ttgtcagcca gatcttctcg cctcatatgc tccccatagg tattgtcgcc    480
gccaatgctc gcatatttga gagagtgata gtgaagaaat atgaaaatga acggtgaagg    540 gattttggc ccgcccttgg gaaaaaacgc acagttcctc gcttgtcccc acacgtgcaa     600
ccccgtggcc tagatgttcc tactcacgtc tgacttcctg gaaatgttcg atcggtcgtt    660
cctccaaact caaactctga gctgctttaa taaatccagc cgcacacgtg tacttcctcc    720
gtctcaaaat aagtagctta ttacaatttt atactaaaac tattacaaag ttgagatagt    780
tattttaaaa tggaggaagt aggtaacaaa gtgggacaaa tttgatcccc acggaattcc    840
tttatctttg caaatccaag caatctaatg gattttctag ggtcaagcat gagtgtgaat    900
taaggatcaa gcaaaacttc tggacagata agcatcaact tgtcagttgt cacagataca    960
cgcatgcgta atgagtcata tacatataca tacgtggcaa aatttcgccc tcgtcacttc   1020
attacgactt ataatcttga cttaaaccca agaattcgca cccagttttt tcatttcagc   1080
aaggcgtttt gcttccattt gttatcccag ctttgctcct ctgtcatcca tggatccacc   1140
catataggaa gatagaaaag gataatcccc ttattgttct tgttgactt tgcatgaaca    1200 aggaaatcag aagataaaca tctagcctag ggagaaggaa ggaatccagc cgagacccac   1260
agtgtcgcca ttggcgacag catagcgtgt aacctaagct gtaaacccct cgggattggg   1320 gaaagggcc gtggtaggac ccaacgatgc ggggcccgtc cattctattc cgtccgttcc     1380
cgtgtcccgt ccagactcag agtgtcccca cacaataatt cgccgacgg atcgtactcc    1440 taccttctc cccccaatac cgggcctgct ctgctactgc agctataaat cccgaccccg     1500
ataggtcgat ggagatgtgg aaatatcggg tcctgggatc ggttgctgcc ctgctcttgc    1560
tgctcgccgt cgtcgtgccg tttactcaga cctggacgca gagcgcgcgg acaaggctg    1620 ccatggcgga agacgcgggg ccgttgatgg gaggcatcga ggactcgccg atgggacaag   1680
agaacgacct cgacgtcatc gcgctcgccc gcttcgccgt ctccgagcac aacaagaagg   1740
ccgtaagccc tcgctatccc cctctctctc tctctcatgt ccatccctgc gagtgaggtc   1800
caactggatc tgagttcgac ggccgggctg ttggatccac agagctttgg tcactggccc   1860
ttctgtagta ttacatcgac gatcgatcta agttaaagtc aaccgccgta aatcatacag   1920
tatgaatctt cgcgattttt gatttaagcc atggcgcctt ttttctcaac aaaaaagaac   1980
acctgaagta tatttgacag gcagcccaac agcaagtgct cctgctagat ttgccggatt   2040
attatttgtt ctaagtatta tccaatacta gtaagttccc catgacaatg gaggtttgtt   2100
agttggattg attttttttg gcgctacccc tgtcacagaa tgccctgctg gagttcgaga   2160
atgtggtgaa gctgaagaaa caaactgttg ctggcaccat gtactacatt acaattcggg   2220
tcactgaagg tgggaccaag aagctctatg aagctaaggt gtgggagaaa ctatgggaga   2280
actttaagca gcttgaggag ttcaagccgg tgcaggacgc tgcaattgca taa          2333
```

<210> SEQ ID NO 16
<211> LENGTH: 31
<212> TYPE: DNA
<213> ORGANISM: Hordeum vulgare

<400> SEQUENCE: 16

```
tatatctaga ctatcggggt cgggatttat a                                     31
```

-continued

```
<210> SEQ ID NO 17
<211> LENGTH: 30
<212> TYPE: DNA
<213> ORGANISM: Hordeum vulgare

<400> SEQUENCE: 17
atataagctt cgaagaggta aaaccctacg                                    30

<210> SEQ ID NO 18
<211> LENGTH: 31
<212> TYPE: DNA
<213> ORGANISM: Hordeum vulgare

<400> SEQUENCE: 18
atataagctt aggttgccat caaggaatag a                                  31

<210> SEQ ID NO 19
<211> LENGTH: 29
<212> TYPE: DNA
<213> ORGANISM: Hordeum vulgare

<400> SEQUENCE: 19
atataagctt cccttaccac tcgctgatg                                     29

<210> SEQ ID NO 20
<211> LENGTH: 29
<212> TYPE: DNA
<213> ORGANISM: Hordeum vulgare

<400> SEQUENCE: 20
atataagctt gcacagttcc tcgcttgtc                                     29

<210> SEQ ID NO 21
<211> LENGTH: 29
<212> TYPE: DNA
<213> ORGANISM: Hordeum vulgare

<400> SEQUENCE: 21
atataagctt aataaatcca gccgcacac                                     29

<210> SEQ ID NO 22
<211> LENGTH: 29
<212> TYPE: DNA
<213> ORGANISM: Hordeum vulgare

<400> SEQUENCE: 22
atataagctt aaaatttcgc cctcgtcac                                     29

<210> SEQ ID NO 23
<211> LENGTH: 30
<212> TYPE: DNA
<213> ORGANISM: Hordeum vulgare

<400> SEQUENCE: 23
atataagctt gcgttttgct tccatttgtt                                    30

<210> SEQ ID NO 24
<211> LENGTH: 30
<212> TYPE: DNA
<213> ORGANISM: Hordeum vulgare

<400> SEQUENCE: 24
atataagctt gcgacagcat agcgtgtaac                                    30
```